US008182804B1

(12) United States Patent
Collins et al.

(10) Patent No.: US 8,182,804 B1
(45) Date of Patent: May 22, 2012

(54) ENGINEERED ENZYMATICALLY ACTIVE BACTERIOPHAGES AND METHODS OF USES THEREOF

(75) Inventors: James J Collins, Newton, MA (US); Hideki Kobayashi, Yokohama (JP); Mads Kearn, Ottawa (CA); Michihiro Araki, Minatoku (JP); Ari Friedland, Boston, MA (US); Timothy Kuan-Ta Lu, Palo Alto, CA (US)

(73) Assignees: Trustees of Boston University, Boston, MA (US); Massachusetts Institute of Technology, Cambridge, MA (US)

(*) Notice: Subject to any disclaimer, the term of this patent is extended or adjusted under 35 U.S.C. 154(b) by 890 days.

(21) Appl. No.: 11/662,551

(22) PCT Filed: Sep. 12, 2005

(86) PCT No.: PCT/US2005/032365
§ 371 (c)(1),
(2), (4) Date: Dec. 21, 2007

(87) PCT Pub. No.: WO2006/137847
PCT Pub. Date: Dec. 28, 2006

Related U.S. Application Data

(60) Provisional application No. 60/609,400, filed on Sep. 13, 2004.

(51) Int. Cl.
*A01N 63/00* (2006.01)
*C12N 15/74* (2006.01)
*A61K 48/00* (2006.01)

(52) U.S. Cl. .................. 424/93.2; 424/93.6; 435/471

(58) Field of Classification Search .................. None
See application file for complete search history.

(56) References Cited

U.S. PATENT DOCUMENTS

| | | | |
|---|---|---|---|
| 5,766,905 A * | 6/1998 | Studier et al. | 435/235.1 |
| 7,758,856 B2 | 7/2011 | Hughes | |
| 2002/0037260 A1* | 3/2002 | Budny et al. | 424/49 |
| 2009/0155215 A1 | 6/2009 | Collins et al. | |
| 2011/0008402 A1 | 1/2011 | Madhyastha et al. | |

FOREIGN PATENT DOCUMENTS

WO    WO 2004/062677 A1    1/2004

OTHER PUBLICATIONS

Sutherland (Carbohydrate Polymers. 1999; 38: 319-328).*
Kim et al. (Applied and Environmental Microbiology. Feb. 2000; 66(2): 788-793).*
Krylov (Russian Journal of Genetics. 2001: 37(7): 715-730).*
Rosenberg et al. (inNovations. Dec 1996; 6: 2-14).*
Willats, W., "Phage display: practicalities and prospects," *Plant Molecular Biology* 50:837-854, 2002.
Beck et al. J. Back. 173:947-954; 1991.
Shuren, J. (2006), ed. U.S. Food and Drug Administration, H (Federal Register, vol. 71, pp. 47729-47732.
Studier, F.W. and Dunn, J.J., "Organization and Expression of Bacteriophage T7DNA." Cold Spring Harb Symp Quant Biol. 47(PT2) 999-1007, 1893.
Studier, F.W., "bacteriophage T7." Science 176:367-376, 1972.
Anderson, JC et al., "Environmentally Controlled Invasion of Cancer Cells by Engineered Bacteria." J. Mol. Biol. 355:619-627, 2006.
Andrianantoandro, E et al., "Synthetic biology: new engineering rules for an emerging discipline." Molecular Systems Biology 2:2006.0028:1-14, 2006.
Aslam, S et al., "Treatment of Clostridium difficile-associated disease: old therapies and new strategies." Lancent Infect Dis 5:549-557, 2005.
Boratynski, J et al., "Preparation of Endotoxin-free Bacteriophages." Cellular and Molecular Biology Letters 9:253-259, 2004.
Ceri, H et al., "The Calgary Biofilm Device: New Technology for Rapid Determination of Antibiotic Susceptibilities of Bacterial Biofilms." Journal of Clinical Microbiology 37(6):1771-1776, 1999.
Chan, Ly et al., "Refactoring bacteriophage T7." Molecular Systems Biology Sep. 13: 1-10, (2005).
Costerton, JW et al., "Bacterial Biofilms: A Common Cause of Persistent Infections." Science 284:1318-1322, 1999.
Curtin, JJ et al., "Using Bacteriophages to Reduce Formation of Catheter-Associated Biofilms by *Staphylococcus epidermis*." Antimicrobial Agents and Chemotherapy 50(4):1268-1275, 2006.
Datsenko, KA and BL Wanner, "One-step inactivation of chromosomal genes in *Escherichia coli* K12 using PCR Products." PNAS 97(12):6640-6645, 2000.
Davey, ME and GA O'Toole, "Microbial Biofilms: from Ecology to Molecular Genetics." Microbiology and Molecular Biology Reviews 64(4):847-867, 2000.
Doulatov, S et al., "Tropism switching in Bordetella bacteriophage defines a family of diversity-generating retroelements." Nature 431:476-481, 2004.
Endy, D, "Foundations for engineering biology." Nature 438:449-453, 2005.
Garcia, LR and IJ Molineux, "Incomplete Entry of Bacteriophage T7 DNA into F Plasmid-Containing *Escherichia coli*." Journal of Bacteriology 177(14):4077-4083, 1995.
Ghigo, J-M, "Natural conjugative plasmids induce bacterial biofilm development." Nature 412:442-445, 2001.

(Continued)

*Primary Examiner* — Scott Long
(74) *Attorney, Agent, or Firm* — Nixon Peabody LLP; Ronald I. Eisenstein; Leena H. Karttunen Contarino

(57) ABSTRACT

The present invention provides engineered bacteriophages that express at least one biofilm degrading enzyme on their surface and uses thereof for degrading bacterial biofilms. The invention also provides genetically engineered bacteriophages expressing the biofilm degrading enzymes and proteins necessary for the phage to replicate in different naturally occurring biofilm producing bacteria. The phages of the invention allow a method of biofilm degradation by the use of one or only a few administration of the phage because the system using these phages is self perpetuating, and capable of degrading biofilm even when the concentration of bacteria within the biofilm is low.

18 Claims, 5 Drawing Sheets

OTHER PUBLICATIONS

Hagens, S et al., "Therapy of Experimental Pseudomonas Infections with a Nonreplicating Genetically Modified Phage." Antimicrobial Agents and Chemotherapy 48(10):3817-3822, 2004.

Hagens, S and U Bläsi, "Genetically modified filamentous phage as bactericidal agents: a pilot study." Letters in Applied Microbiology 37:318-323, 2003.

Hasty, J et al., "Engineered gene circuits." Nature 420:224-230, 2002.

Hickman-Brenner, FW et al., "Phage Typing of *Salmonella enteritidis* in the United States." Journal of Clinical Microbiology 29(12):2817-2823, 1991.

Hughes, KA et al., "Bacteriophage and associated polysaccharide depolymerases—novel tools for study of bacterial biofilms." Journal of Applied Microbiology 85:583-590, 1998.

Itaya, M et al., "Combining two genomes in one cell: Stable cloning of the Synechocystis PCC6803 genome in the *Bacillus subtilis* 168 genome." PNAS 102(44):15971-15976, 2005.

Itoh, Y et al., "Depolymerization of β-1,6-N-Acetyl-D-Glucosamine Disrupts the Integrity of Diverse Bacterial Biofilms." Journal of Bacteriology 187(1):382-387, 2005.

Hoffman, LR et al., "Aminoglycoside antibiotics induce bacterial biofilm formation." Nature 436:1171-1175, 2005.

Hughes, KA et al., "Biofilms susceptibility to bacteriophage attack: the role of phage-borne polysaccharide depolymerase." Microbiology 144:3039-3047, 1998.

Jackson, DW et al., "Biofilm Formation an Dispersal under the Influence of the Global Regulator CsrA of *Escherichia coli*." Journal of Bacteriology 184(1):290-301, 2002.

Kolter, R and EP Greenberg, "The superficial life of microbes." Nature 441:300-302, 2006.

Liu, M et al., "Reverse Transcriptase-Mediated Tropism Switching in Bordatella Bacteriophage." Science 295:2091-2094, 2002.

Loose, C et al., "A linguistic model for the rational design of antimicrobial peptides." Nature 443:867-869, 2006.

Merril, CR et al., "The prospect for bacteriophage therapy in Western medicine." Nature Reviews 2:489-497, 2003.

Merril, CR et al., "Longe-circulating bacteriophage as antibacterial agents." Proc. Natl. Acad. Sci. USA 93:3188-3192, 1996.

Parsek, MR and PK Singh, "Bacterial Biofilms: An Emerging Link to Disease Pathogenesis." Annu. Rev. Microbiol. 57:677-701, 2003.

Projan, S, "Phage-inspired antibiotics?" Nature Biotechnology 22(2):167-168, 2004.

Re, SD et al., "Tight Modulation of *Escherichia coli* Bacterial Biofilm Formation through Controlled Expression of Adhesion Factors." Applied and Environmental Microbiology 73(10):3391-3403, 2007.

Ro, D-K et al., "Production of the antimalarial drug precursor artemisinic acid in engineered yeast." Nature 440:940.943, 2006.

Scholl, D et al., "*Escherichia coli* K1's Capsule is a Barrier to Bacteriophage T7." Applied and Environmental Microbiology 71(8):4872-4874, 2005.

Schoolnik, GK et al., "Phage offer a real alternative." Nature Biotechnology 22(5)505-507, 2004.

Stewart, PS and JW Costerton, "Antiobiotic resistance of bacteria in biofilms." The Lancet 358:135-138, 2001.

Summers, WC, "Bacteriophage Therapy." Annu. Rev. Microbiol. 55:437-451, 2001.

Tian, J et al., "Accurate multiplex gene synthesis from programmable DNA microchips." Nature 432:1050-1054, 2004.

Wentworth, BB, "Bacteriophage Typing of the *Staphylococci*." Bacteriol Rev 27: 253-272, 1963.

Whitchurch, CB et al., "Extracellular DNA Required for Bacterial Biofilm Formation." Science 295:1487, 2002.

Xavier, JB et al., "Biofilm-control strategies based on enzymic disruption of the extracellular polymeric substance matrix—a modeling study." Microbiology 151:3817-3832, 2005.

Baker, D. et al., "Engineering Life: Building a FAB for Biology." Sci Am. 294(6):44-51, 2006.

Bartlett, J. G., MD, "Narrative Review: The New Epidemic of Clostridium difficile—Associated Enteric Disease." Ann. Intern. Med. 145:758-764, 2006.

Corbin, B. D. et al., "Bacteriophage T4 multiplication in a glucose-limited *Escherichia coli* biofilm." Can. J. Microbiol. 47:680-684, 2001.

Costerton, J. W. and Lewandowski, Z., "Microbial Biofilms." Annu. Rev. Microbiol. 49:711-745, 1995.

Doolittle, M.M. et al., "Tracing the interaction of bacteriophage with bacterial biofilms using fluorescent and chromogenic probes." Journal of Industrial Microbiology 16:331-341, 1996.

Doolittle, M. M. et al., "Lytic infection of *Escherichia coli* biofilms by bacteriophage T4." Can. J. Microbiol. 41:12-18, 1995.

Dunn, J. J. and Studier, F. W. "Complete Nucleotide Sequence of Bacteriophage T7 DNA and the Locations of T7 Genetic Elements." J. Mol. Biol. 166:477-535, 1983.

Kaplan et al. J. Bact. 186 (24): 8213-8220, 2001.

Slootweg et al. Nucleic Acids Res. Oct. 13, 2006, e1-11.

* cited by examiner

ENGINEERED ENZYMATICALLY ACTIVE BACTERIOPHAGES AND METHODS OF USES THEREOF

CROSS-REFERENCE TO RELATED APPLICATIONS

This application is a 371 National Phase Entry Application of co-pending International Application PCT/US2005/032365, filed Sep. 12, 2005, which designated the U.S. and claims benefit under 35 U.S.C. 119(e) of U.S. provisional application No. 60/609,400, filed Sep. 13, 2004, the content of which is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Feb. 6, 2012, is named 71586782.txt and is 16,539 bytes in size.

GOVERNMENT SUPPORT

This invention was made with Government Support under Grant No. DE-AC05-00OR22725 awarded by the Department of Energy, and Grant No. EIA-0130331 awarded by the National Science Foundation. The United States Government has certain rights in the invention.

BACKGROUND OF THE INVENTION

Bacterial biofilms are sources of contamination that are difficult to eliminate in a variety of industrial, environmental and clinical settings.

Biofilms are polymer structures secreted by bacteria to protect bacteria from various environmental attacks, and thus result also in protection of the bacteria from disinfectants and antibiotics. Biofilms may be found on any environmental surface where sufficient moisture and nutrients are present. Bacterial biofilms are associated with many human health and environmental problems. For instance, bacteria form biofilms on implanted medical devices, e.g., catheters, heart valves, joint replacements, and damaged tissue, such as the lungs of cystic fibrosis patients. Bacteria in biofilms are highly resistant to antibiotics and host defenses and consequently are persistent sources of infection. Biofilms also contaminate surfaces such as water pipes and the like, and render also other industrial surfaces hard to disinfect.

For example, catheters, in particular central venous catheters (CVCs), are one of the most frequently used tools for the treatment of patients with chronic or critical illnesses and are inserted in more than 20 million hospital patients in the USA each year. Their use is often severely compromised as a result of bacterial biofilm infection which is associated with significant mortality and increased costs. Catheters are associated with infection by many biofilm forming organisms such as *Staphylococcus epidermidis, Staphylococcus aureus, Pseudomonas aeruginosa, Enterococcus faecalis* and *Candida albicans* which frequently results in generalized blood stream infection. Approximately 250,000 cases of CVC-associated bloodstream infections occur in the US each year with an associated mortality of 12%-25% and an estimated cost of treatment per episode of approximately $25,000. Treatment of CVC-associated infections with conventional antimicrobial agents alone is frequently unsuccessful due to the extremely high tolerance of biofilms to these agents. Once CVCs become infected the most effective treatment still involves removal of the catheter, where possible, and the treatment of any surrounding tissue or systemic infection using antimicrobial agents. This is a costly and risky procedure and re-infection can quickly occur upon replacement of the catheter.

Bacteriophages (phage) and their therapeutic uses have been the subject of much interest since they were first recognized early in the 20th century. Lytic bacteriophages are viruses that infect bacteria exclusively, replicate, disrupt bacterial metabolism and destroy the cell upon release of phage progeny in a process known as lysis. These bacteriophages have very effective antibacterial activity and in theory have several advantages over antibiotics. Most notably they replicate at the site of infection and are therefore available in abundance where they are most required; no serious or irreversible side effects of phage therapy have yet been described and selecting alternative phages against resistant bacteria is a relatively rapid process that can be carried out in days or weeks.

Bacteriophages have been used to destroy biofilms (e.g., U.S. Pat. No. 6,699,701). Also, systems using bacteriophages that encode biofilm destroying enzymes in general have been described. Art also provides a number of examples of lytic enzymes encoded by bacteriophages that have been used to destroy bacteria (U.S. Pat. No. 6,335,012 and U.S. Patent Application Publication No. 2005/0004030).

Specifically, in one embodiment, PCT Publication No. WO 2004/062677 provides a method of treating bacterial biofilm, wherein the method comprises use of a first bacteriophage capable of infecting the bacteria within the biofilm and wherein the bacteriophage also encodes a polysaccharide lyase enzyme that is capable of degrading polysaccharides in the biofilm. In one embodiment, additional enzyme is absorbed on the surface of the phage.

However, even when the phage of WO 2004/062677 is delivered with an enzyme mixture or with an enzyme "associated" or "absorbed" on the surface of the first phage dose, the method requires that after the initial administration, the phage released from the destroyed bacterial must "find" and infect at least one additional bacterium to enable it to continue to degrade the biofilm. Therefore, WO 2004/062677 specifically discusses the benefits of using multiple dosages of phage administration to enhance the results (see, e.g., page 14, lines 6-10). Such multiple administration is not always possible or practical.

Moreover, the requirement for the phage to find and infect bacteria before it can destroy the surrounding biofilm provides a formidable obstacle when the bacterial concentration in the biofilm is low or when most of the bacteria have been destroyed and some bacterial isolates are still protected by a large mass of biofilm.

Therefore, there is a need for improved phages to degrade biofilm.

SUMMARY OF THE INVENTION

The invention is based upon the discovery that a genetically engineered bacteriophage that encodes a biofilm destroying enzyme and displays such enzyme on its surface, as opposed to being mixed with an enzyme or encoding an enzyme that is released from the cell, can be used to efficiently degrade and destroy biofilms. This construction provides phages and uses thereof that provide method for a continuous biofilm degradation system, i.e., one that will replicate itself, with fewer or no need for multiple dosages.

The engineered phage expressing and displaying a biofilm degrading enzyme can be used to treat diseases, such as cystic fibrosis, in which biofilm formation prevents efficient treatment of bacterial infections with conventional antibiotics. The phages of the invention are further useful in clearing off biofilm from various other surfaces, such as water pipes, catheters, and other surfaces that are often contaminated by bacteria forming a protective biofilm to prevent traditional antimicrobial substances from working properly.

Accordingly, in one embodiment, the invention provides a method of removing biofilm by exposing the biofilm and bacteria contained therein to a bacteriophage which encodes and displays on its surface an enzyme capable of degrading one or more components present in a biofilm. The bacteriophage is also capable of infecting the biofilm secreting bacteria.

One particular benefit of the bacteriophage displaying biofilm degrading enzyme on its surface and method of using it according to the invention is the phage's capacity to continue destroying biofilm even in an environment where the concentration of bacteria is low, i.e., it has the ability to perpetuate itself. This is because the phage released from the lysed bacteria express the enzyme on their surface, and can therefore digest their way through further biofilm even if there are no bacteria in the vicinity for the phage to re-infect.

The invention further provides improved genetically engineered phages for destruction of biofilm.

BRIEF DESCRIPTION OF FIGURES

FIG. 2A shows crystal violet absorbance after treatment with ampicillin, cellulase, phage T7 and enzymatic phage for 24 hours. The absorbance values are expressed relative to that of untreated biofilm after subtraction of the absorbance value of a sterile well (negative control). FIG. 2B shows absorbance after different periods of treatment with enzymatic phage (closed circles) or no treatment (open circles), normalized by the time-averaged absorbance of untreated biofilm after subtraction of the absorbance value of a sterile well. The solid curve is drawn to guide the eye. FIG. 2C shows photographs of glass plates extracted from a microfermenter, before and after 6-hour treatment with enzymatic phage. FIG. 2D shows counts of colony forming units (CFU) after the indicated treatment for 6 hours. Conditions are otherwise the same as in FIG. 2A.

DETAILED DESCRIPTION OF THE INVENTION

Figure 1:
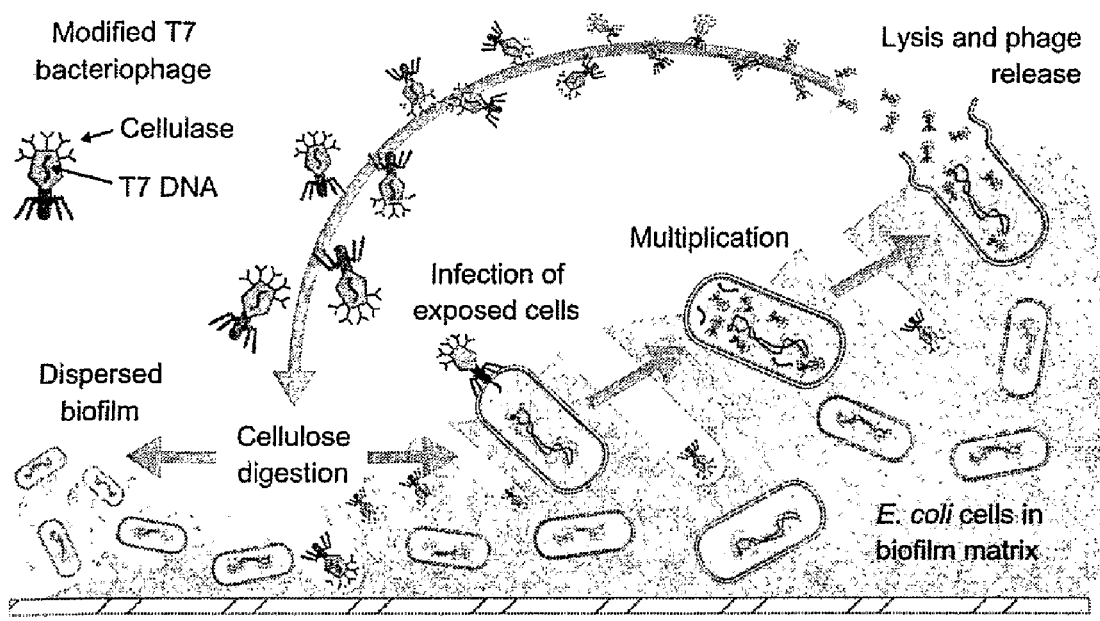
FIG. 1 shows the strategy for biofilm reduction by the enzymatically active bacteriophage. The engineered phage T7 degrade the extracellular matrix of the biofilm, thus exposing the biofilm-embedded cells and facilitating phage infection. After infection, the phage multiply and lyse the host cell, releasing additional enzymatic phage in the process.

We have discovered and produced engineered bacteriophages that express at least one biofilm degrading enzyme on their surface. We have also discovered that by further genetically engineering the bacteriophages expressing the biofilm degrading enzymes, the phages can replicate in most biofilm producing bacteria. The phages of the invention allow a method of biofilm degradation by the use of one or only a few administrations of the engineered phage because the system using these phages is self perpetuating, and capable of degrading biofilm even when the concentration of bacteria within the biofilm is low. This is a significant advantage to prior art which describes essentially two types of phage-enzyme combinations. First, phages that are mixed with enzymes that can degrade the biofilm essentially only before infection by the phage. The enzymes are then rapidly diluted as the phage multiplies. Second, phages that encode biofilm degrading enzymes and allow intracellular production of the enzymes. In such a system, the enzyme is diffused from the lysed cell only to close proximity of the lysed cell and thus does not allow the phage to travel through a thick biofilm to reach another cell to infect. The present invention avoids the dilution problem by producing phages with the active enzyme displayed on their surface. It also avoids the problem of the phage being trapped within a thick biofilm with no bacteria within its reach to infect and lyse.

The bacteriophage of the invention encodes an enzyme or portion thereof that is displayed on the surface of the phage. Consequently, the phage has an active enzyme portion on its surface that will degrade the biofilm. Thereafter, when the phage encounters a bacterial cell, the phage will replicate. After the phage enters the cell for replication in addition to the normal phage components that are needed for replication in the cell, there will also be the enzyme and a "moiety", typically a capsid protein, or a capsid attaching part of such capsid protein fused to the enzyme or an active portion of the enzyme directing the enzyme to the phage surface. Thus after the multiplication and lysis of the cell by the phage a new generation of these enzyme displaying phages are produced. These in turn will digest additional biofilm and can replicate in subsequent bacterial cells thus creating a virtually perpetual or continual system for biofilm degradation and destruction. Each new generation of phages carries the biofilm degrading enzyme allowing the phage to attack the biofilm from outside, by the action of the enzyme, and lyse the bacteria from inside, by the action of phage infecting the bacterium, multiplification of the phage, and consequent cell lysis.

The "moieties" that can be used to direct and attach the biofilm degrading enzyme to the phage surface according to the present invention include, for example, moieties that are commonly used in the phage display techniques, that are well known to one skilled in the art. For example, the enzyme can be part of the other part of a fusion protein, wherein the other part of the fusion protein is part of the surface of the phage such as the capsid, for example, a 10B capsid protein. For example, the 10B capsid protein makes up about 10% of the capsid protein of T7 phage. Proteases can be displayed on the surface of the phage as described by Atwell S and Wells JA (Selection for improved subtiligases by phage display. Proc Natl Acad Sci USA. 1999. 96(17):9497-502). Atwell and Wells describe a system where about 16-17 amino acids of active sites of the protease were displayed on the phage and showed protease activity. Accordingly, one useful amino acids sequence is signal peptide-XXX-SEGGGSEGGG-XX (SEQ ID NO.: 54) (X is optional, or any amino acid). Another example of useful moieties is a xylan binding domain of xylanase (Miyakubo H, Sugio A, Kubo T, Nakai R, Wakabayashi K, Nakamura S. Phage display of xylan-binding module of xylanase J from alkaliphilic *Bacillus* sp. strain 41M-1.

Nucleic Acids Symp Ser. 2000. (44):165-6). In Miyakubo et al., the moiety displayed on the phage was not the active site of the enzyme but the substrate binding site of the enzyme, which also retained its capacity to bind the substrate.

Accordingly, the present invention provides essentially perpetually or continually biofilm degrading bacteriophages and uses thereof in degrading biofilm.

Naturally, in addition to displaying at least one enzyme on its surface the phage may also encode an enzyme that is not displayed on the surface. It is well recognized that the requirement of finding and infecting bacteria provide an obstacle when the bacterial concentration in the biofilm is low or when most of the bacteria have been destroyed and some bacterial isolates are still protected by a large mass of biofilm.

The present invention describes a biofilm degrading phage system, wherein essentially one dosage of infection is sufficient to allow complete destruction of biofilm, because the infected bacteria produce phages that contain the enzymatic activity on their surface. This allows the phage themselves to continue degrading the biofilm even in the absence of immediately infectable bacteria in the environment. This solves a persistent re-application problem presented by the previously described phage systems. For example, even when the phage of WO-2004/062677 is delivered with an enzyme mixture or with an enzyme "associated" or "absorbed" on the surface of the first phage dose, the method requires that after the initial administration, the phage released from the destroyed bacterial must "find" and infect at least one additional bacterium to enable it to continue to degrade the biofilm. Therefore, WO 2004/062677 specifically discusses the need for using multiple dosages of phage administration to enhance the results.

A phage, also referred to as a bacteriophage, is a small virus that infects only bacteria. Bacteriophage are the natural enemies of bacteria and, over the course of evolution, have developed proteins which enable them to infect a bacterial host cell, replicate their genetic material, usurp host metabolism, and ultimately kill their bacterial host cell. Like viruses that infect eukaryotes, phages consist of an outer protein hull and the enclosed genetic material, which consists of double-stranded DNA in 95% of the phages known, of 5 to 650 kbp (kilo base pairs) with a length of about 24 to 200 nm. The vast majority of phages (about 95%) have a tail to let them inject their genetic material into the host.

The phages of the present invention can be designed to be specific for any selected strain of bacteria, thus desirable bacteria can be spared. Bacteriophage specific for a single bacterial host in nature have been found to remain within the host for as long as the bacterial host specific for that phage is present. For example, Weber-Dabrowska, et al. (1987), Arch Immunol Ther Exp (Warsz) 35(5):563-8, tested for absorption of orally administered anti-staphylococcal and anti-pseudomomas phage in both urine and serum samples of patients with suppurative bacterial infections. No phage was present in any of the 56 patients prior to phage therapy. By day 10, 84% of the serum samples and 35% of urine samples contained phage, indicating bioavailability. The healthy control group exhibited a phage titer drop 100-fold between days 0-5. A comprehensive review of phage therapy (Alisky et al. (1998), J of infection 36:5) concluded that all studies with both human and animals showed no measurable antiphage antibodies generated.

The phages of the present invention degrade biofilm by simultaneously degrading the extracellular biofilm matrix, and infecting and lysing biofilm-embedded cells.

In one embodiment, the invention provides bacteriophages that have been genetically engineered to express at least one biofilm degrading enzyme on their surface. The theoretical boundaries of enzyme copy number per phage depend primarily on the size of the enzyme and the number of capsid proteins per phage. Generally, the number of enzymes displayed on the phage is dependent on the number of capsid protein of the phage. For example in T7, one can use one fusion protein in the case of a large enzyme, or as many as 415 in the case of a small enzyme or enzymatically active fragment. Preferably, each phage has multiple copies for the biofilm degrading enzyme, or a biofilm degrading fragment of an enzyme on their surface. The phage can carry, for example, 1 copy, 2, 3, 4, 5, 6, 7, 8, 9, 10, 11, 12, 13, 14, 15, 16, 17, 18, 19, 20 copies, 20-50, 50-100, 100-200, 200-300, 300-400, 400-500 or more, of enzyme or an active fragment thereof on their surface. Wild type T7 has a capsid that is composed of 10% of 10B, a small capsid protein. One can make a fusion protein with this capsid protein and the enzyme. For example, 10B plus about 40 to 50 amino acids encoding the active or biding site of an enzyme. In an alternative embodiment, one could theoretically replace every capsid protein. However, a larger one, for example 10B plus up to about 1000 amino acids long enzyme, will sterically hinder the self assembly process and have to be diluted with the smaller wild type capsid proteins. Typically, the engineered phage carries about 5-15 copies of enzyme on its surface. For example, in one embodiment, the enzyme, e.g. a protease fusion protein with 10B capsid protein could be displayed on the phage surface.

The bacteriophage can be any phage that has the capacity to infect a biofilm producing bacterium, such as *E. coli, P. aeriginosa, S. aureus, E. fecalis* and the like. Such phages are well known to one skilled in the art, and include, but are not limited to, lambda phages, T7, T3, and T-even and T-even like phages, such as T2, and T4, and RB69; also phages such as Pf1, Pf4, *Bacteroides fragilis* phage B40-8 and coliphage MS-2 can be used. For example, lambda phage attacks *E. coli* by attaching itself to the outside of the bacteria and injecting its DNA into the bacteria. Once injected into its new host, the phage uses *E. Coli*'s genetic machinery to transcribe its genes. Any of the known phages can be engineered to express a biofilm degrading enzyme on its surface, as described herein.

The bacteriophages of the present invention are engineered using the traditional methods of genetic engineering that are well known to one skilled in the art. Based on the sequences provided herein and others known to one skilled in the art, one can readily prepare and produce the phages of the invention. Many of the examples at the end of this specification use T7 phage and provide one illustration of engineering the phages of the invention. However, the same principles can be used to create any other phage known to one skilled in the art, such as lambda phages, T3, and other T-odd and T-even like phages, such as T2, T4 and RB69; and Pf1, Pf4, *Bacteroides fragilis* phage B40-8 and coliphage MS-2.

In one embodiment, the phage encodes at least one enzyme that is capable of degrading biofilm selected from the group consisting of aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, xylanase or lyase, wherein the enzyme is an integral part of the coat of the virus. In one embodiment, one enzyme per phage is expressed.

In one embodiment, the enzyme is selected from the group consisting of cellulases, such as glycosyl hydroxylase family of cellulases, such as glycosyl hydroxylase 5 family of enzymes also called cellulase A; polyglucosamine (PGA) depolymerases; and colonic acid depolymerases, such as 1,4-L-fucodise hydrolase (see, e.g., Verhoef R. et al., Characterisation of a 1,4-beta-fucoside hydrolase degrading colanic acid, Carbohydr Res. 2005 Aug. 15; 340(11):1780-8), depolymerazing alginase, and DNase I, or combinations thereof.

For example, an enzymatic phage displaying the enzyme on its surface can be engineered using lambda phages, T7, T3, and other T-odd and T-even like phages, such as T2, T4 and RB69; also phages such as Pf1, Pf4, *Bacteroides fragilis* phage B40-8 and coliphage MS-2. For example, a T7 phage called T7Select System (Novagen Inc., Darmstadt, Germany) can be used. The celA gene from *C. thermocellum* can be isolated by PCR using, for example, primers 5'-catg aat tcT GCA GGT GTG CCT TTT AAC ACA AAA TAC-3' (SEQ ID NO:1) and 5'-gac gtc aag ctt TTT CCG TAA ATC TGT CAA AAA CCC ATT ACA 3' (SEQ ID NO:2), and it can be cloned into the T7 genome, for example, via EcoRI and HindIII sites.

The selection of enzyme naturally also depends on the type of biofilm to be targeted, and a skilled artisan can readily determine the enzyme based on the components of biofilm produced by specific bacteria. For example, it is known that *E. coli* biofilm comprises cellulose, therefore a phage specific to *E. coli*, such as lambda phages, T7, T3, and other T-even and T-even like phages, such as T2, T4 and RB69, can be engineered to express on its surface a gene cellulase enzyme.

Similarly, it is known that one of the major components of *P. aeruginosa* biofilm is alginate, accordingly a phage specific to *P. aeruginosa* can be engineered to express on its surface, for example an alginase enzyme. Combination of phages expressing these two enzymes can be used to target a dual biofilm comprising both *E. coli* and *P. aeruginosa*.

In one embodiment, the enzyme is a cellulase or cellulolytic enzyme, which refers to an enzyme produced, for example, by certain bacteria which catalyses the degradation of cellulose to glucose, cellobiose, triose and other cellooligosaccharides. The cellulase can be an endoglucanase, a microbial endoglucanase, especially a bacterial endoglucanase. Endocellulases attack cellulose chains at positions away from the ends, whereas exocellulases degrade the chains from one end. Both endo- and exocellulases can be used in the present invention. Beta-glucosidases form a third general group of cellulases useful according to the present invention. Also cellobiohydrolases and cellobiases can be used. The cellulase or endoglucanase may be an acid, neutral, or alkaline cellulase or endoglucanase, i.e., exhibiting maximum cellulolytic activity in the acid, neutral or alkaline pH range, respectively. In one preferred embodiment, the cellulase is a bacterial cellulase.

In one embodiment, the cellulase is cellulase A encoded by celA gene of *Clostridium thermocellum*.

In one embodiment, the enzyme is selected from the group consisting of enzymes, for example, cellulases, encoded by the nucleic acids listed in Table 1.

TABLE 1

Public nucleic acid accession numbers of useful enzymes

X79241: *Pectobacterium carotovorum* celV1 gene for cellulase
gi|68644817|emb|X79241.2|ECCELV1[68644817]
S55178: endA = cellulase[*Ruminococcus flavefaciens*, strain 17, Genomic, 1600 nt]
gi|234871|bbm|148732|bbs|55178|gb|S55178.1|[234871]
X65616: *S. reticuli* cell gene for mycelium-associated cellulase (avicelase 1)
gi|683711|emb|X65616.1|SRCEL1G[683711]
AB028321: *Ruminococcus albus* cel5D, cel9A genes for beta-1,4-endoglucanase VII, cellulase VI, complete cds, gi|15430618|dbj|AB028321.2|[15430618]
Y17552: *Alteromonas haloplanctis* cel G gene
gi|3687411|emb|Y17552.1|AHY17552[3687411]
Z34519: *Bacillus subtilis* 168 trpC2 xynA gene encoding xylanase
gi|2995396|emb|Z34519.1|BSXYLAN[2995396]
Z86105: *A. thermophilum* celA gene and manA pseudogene
gi|2437818|emb|Z86105.1|ATZ86105 [2437818]
Y12512: *Bacillus* sp. BP23 celA gene, gi|1945639|emb|Y12512.1|BSPY12512[1945639]
Z83304 : *R. flavefaciens* endA gene, gi|1915943|emb|Z83304.1|RFENDA[1915943]
Z86104 : *A. thermophilum* celB gene and celC pseudogene,
gi|1865684|emb|Z86104.1|ATZ86104[1865684]
Z69341: *T. maritima* celA and celB gene, gi|1297060|emb|Z69341.1|TMCELAB[1297060]
Z69359: *C. stercorarium* celY and celZ genes,
gi|1181132|emb|Z69359.1|CSCELYZ[1181132]
X76726: *S. aurantiaca* gene for cellulase, gi|895886|emb|X76726.1|SACEL[895886]
X86798: *Cellvibrio japonicus* celE gene, gi|806573|emb|X86798.1|PFCELEGE[806573]
Z46862: *Bacillus subtilis* bglS gene for beta-1,3-1,4-glucanase,
gi|599673|emb|Z46862.1|BSBGLS[599673]
Z29076: *Bacillus subtilis* eglS gene for endo-1,4-beta-glucanase, strain 168 trpC2,
gi|509266|emb|Z29076.1|BSEGLSG[509266]
X51944: *Ruminococcus flavefaciens* celA gene for cellodextrinase (EC 3.2.1.91),
gi|457800|emb|X51944.1|RFCELA[457800]
X76000: *E. carotovora* celV gene for endoglucanase,
gi|434941|emb|X76000.1|ECCELV[434941]
X73953: *S.rochei* eglS gene, gi|393391|emb|X73953.1|SREGLS[393391]
X55299: *C. stercorarium* celZ gene for endo-beta-1,4-glucanase (Avicelase I)
gi|296790|emb|X55299.1|CSCELZ[296790]
X61008: *Streptomyces* sp. casA gene for carboxymethylcellulase,
gi|47520|emb|X61008.1|SSCASAG[47520]
Z12157: *S. halstedii* celA1 gene for endoglucanase,
gi|47132|emb|Z12157.1|SHCEL1G[47132]
X12570: *Cellvibrio japonicus* carboxymethylcellulase (CMCase) gene,
gi|45503|emb|X12570.1|PFCMCASE[45503]
X52615: *Cellvibrio japonicus* celB gene for endoglucanase B,
gi|45497|emb|X52615.1|PFCELB[45497]

TABLE 1-continued

Public nucleic acid accession numbers of useful enzymes

X69390: *C. thermocellum* gene for endo-1,4-beta-glucanase,
gi|40677|emb|X69390.1|CTCELG[40677]
X60545: *C. thermocellum* celF gene for endo-1,4-beta-glucanase
gi|40675|emb|X60545.1|CTCELFG[40675]
X03592: *Clostridium thermocellum* celB gene for endoglucanase B
gi|40668|emb|X03592.1|CTCELB[40668], X67044: *B. subtilis* gene for cellulase
gi|39776|emb|X67044.1|BS14GLUC[39776]
X17538: *Butyrivibrio fibrisolvens* end1 gene for endoglucanase,
gi|39472|emb|X17538.1|BFEND1[39472]
AJ786638: *Bacillus licheniformis* celC gene (partial), celB gene and ydhT gene (partial),
gi|57335431|emb|AJ786638.1|[57335431]
AJ622824: Uncultured bacterium cel gene for putative cellulase, clone LS4,
gi|56675037|emb|AJ622824.1|[56675037]
AJ616005: *Bacillus licheniformis* scdA gene (partial), fenH gene, celA gene, ynfE gene and
ORF1 (partial), gi|56310537|emb|AJ616005.1|[56310537]
AJ488933: *Paenibacillus* sp. BP-23 cel48C gene for cellulose 1,4-beta-cellobiosidase
gi|21449823|emb|AJ488933.1|PAE488933[21449823]
AJ308623: *Alicyclobacillus acidocaldarius* celA gene for cellulase,
gi|13274206|emb|AJ308623.1|AAC308623[13274206]
AJ133614: *Bacillus* sp. BP23 celB gene, gi|4490765|emb|AJ133614.1|BSP133614[4490765]
A28172: *B. lautus* strain NCIM 40250 endocellulase 2 gene (Endo2),
gi|905295|emb|A28172.1||pat|WO|9110732|3[905295]
AJ622825: Uncultured bacterium cel gene for putative cellulase, clone SS24
gi|56675039|emb|AJ622825.1|[56675039]
Z94045: *C. stercorarium* bglZ gene, gi|1938209|emb|Z94045.1|CSBGLZ[1938209]
AJ863163: *Clostridium thermocellum* celY gene for 1,4-beta-glucanase,
gi|55818862|emb|AJ863163.1|[55818862]
AY766381: *Bacillus* sp. HY2-3 cellulase (cel1) gene, complete cds
gi|54402406|gb|AY766381.1|[54402406]
AY445620: *Bacillus licheniformis* strain GXN151 cellulase (cel9A) gene, complete cds
gi|39636953|gb|AY445620.1|[39636953]
AY291066: *Bacillus licheniformis* endo-beta-1,4-glucanase (cel12A) gene, complete cds
gi|31335246|gb|AY291066.1|[31335246]
AY339624: *Bacillus pumilus* endoglucanase A precursor (EglA) gene, complete cds
gi|37498961|gb|AY339624.1|[37498961]
AF105330: *Clostridium cellulovorans* ATP-dependent DNA helicase A (helA) gene, partial
cds; and endoglucanase Y (engY), pectate lyase A (pelA), pectate lyase-related protein
(pelB), and putative nicotinic acid phosphoribosyltransferase genes, complete cds,
gi|52222505|gb|AF105330.2|[52222505]
AY665770: *Bacillus* sp. HB102 endo-beta-1,4-glucanase (gluY) gene, complete cds
gi|51599287|gb|AY665770.1|[51599287]
AJ537597: *Bacillus agaradhaerens* cel gene for putative cellulase
gi|50871763|emb|AJ537597.1|BAG537597[50871763]
AJ537596: Uncultured bacterium cel gene for cellulase, from Lake Nakuru,
gi|50871761|emb|AJ537596.1|UNK537596[50871761]
AJ537595: Uncultured bacterium cel gene for cellulase, from Lake Sonachi,
gi|50871759|emb|AJ537595.1|UNK537595[50871759]
AY632898: *Ruminococcus albus* cellulase (cel5G) gene, complete cds,
gi|48994861|gb|AY632898.1|[48994861]
U12011: Unidentified bacterium clone pFGH1 cellulase (cel) gene, complete cds; and beta-
glucosidase (bgl) gene, partial cds, gi|515666|gb|U12011.1|UBU12011[515666]
AY227046: *Rhizobium leguminosarum* bv. *trifolii* cellulase (cel8A) gene, complete cds,
gi|29293695|gb|AY227046.1|[29293695]
AY551322: *Pseudoalteromonas* sp. MB-1 cellulase (celA) gene, complete cds,
gi|45356856|gb|AY551322.1|[45356856]
AY374129: *Bacteroides cellulosolvens* cellulosomal family-48 processive glycoside
hydrolase precursor, gene, complete cds, gi|38532131|gb|AY374129.1|[38532131]
AX923058: Sequence 2 from Patent EP1350843,
gi|40216145|emb|AX923058.1||pat|EP|1350843|2[40216145]
AY183475: *Bacillus subtilis* cellulase C (celC) gene, complete cds,
gi|37730884|gb|AY183475.1|[37730884]
AJ551527: *Alicyclobacillus acidocaldarius* celB gene for cellulase precursor,
gi|29367432|emb|AJ551527.1|AAC551527[29367432]
AY291583: *Bacillus licheniformis* strain GXN151 putative ScdA (scdA), putative FenH
(fenH), and Cel5A (cel5A) genes, complete cds, gi|31580615|gb|AY291583.1|[31580615]
AJ561043: *Rhizobium leguminosarum* bv. *trifolii* celc2 gene for cellulase C2,
gi|30578071|emb|AJ561043.1|RLE561043[30578071]
AY188753: *Pectobacterium carotovorum* subsp. *carotovorum* cellulase (celC) gene, complete
cds, gi|29468586|gb|AY188753.1|[29468586]
BD161114: Alkaline cellulase gene,
gi|27866872|dbj|BD161114.1||pat|JP|2002171987|1[27866872]
X15429: *Cellvibrio japonicus* xynA gene for xylanase A and endoglucanase gene (partial)
gi|45519|emb|X15429.1|PFXYNA[45519]
BD133888: Alkali cellulase gene,
gi|23228833|dbj|BD133888.1||pat|JP|2002085078|1[23228833]
BD016470: Alkaline cellulase gene,
gi|22557646|dbj|BD016470.1||pat|JP|2001231569|2[22557646]

TABLE 1-continued

Public nucleic acid accession numbers of useful enzymes

BD016469: Alkaline cellulase gene,
gi|22557645|dbj|BD016469.1||pat|JP|2001231569|1[22557645]
AB044407: *Clostridium thermocellum* celT gene for endoglucanase, complete cds
gi|18148435|dbj|AB044407.2|[18148435]
E09719: DNA encoding precursor protein of alkaline cellulase,
gi|22026348|dbj|E09719.1||pat|JP|1995203960|1[22026348]
AX467608: Sequence 18 from Patent WO0234926,
gi|21900796|emb|AX467608.1||pat|WO|0234926|18[21900796]
AX467606: Sequence 16 from Patent WO0234926,
gi|21900794|emb|AX467606.1||pat|WO|0234926|16[21900794]
AX467598: Sequence 8 from Patent WO0234926,
gi|21900786|emb|AX467598.1||pat|WO|0234926|8[21900786]
AX467596: Sequence 6 from Patent WO0234926,
gi|21900784|emb|AX467596.1||pat|WO|0234926|6[21900784]
AX467594: Sequence 4 from Patent WO0234926,
gi|21900782|emb|AX467594.1||pat|WO|0234926|4[21900782]
AF233448: *Sinorhizobium meliloti* endoglucanase precursor (endS) gene, complete cds,
gi|12005273|gb|AF233448.1|[12005273]
AY074776: *Pseudomonas fluorescens* OprQ (oprQ) gene, partial cds; fabG pseudogene,
complete sequence; tRNA-Thr gene, complete sequence; cellulose biosynthesis operon,
complete sequence; and unknown gene, gi|18535629|gb|AY074776.1|[18535629]
AF282321: *Pectobacterium chrysanthemi* endo-1,4-beta-D-glucanase precursor (cel8Y) gene,
complete cds, gi|12240048|gb|AF282321.1|[12240048]
AY077754: *Clostridium cellulolyticum* beta-1,4-glucanase (cel5I) gene, complete cds,
gi|19110247|gb|AY077754.1|[19110247]
AF003697: *Cellvibrio mixtus* cellulase B (celB) gene, complete cds,
gi|18875462|gb|AF003697.2|[18875462]
AF316823: *Clostridium cellulolyticum* cellulase gene cluster, complete sequence,
gi|12007364|gb|AF316823.1|[12007364]
E37675: Thermostable alkaline cellulase gene,
gi|18626785|dbj|E37675.1||pat|JP|2000210081|1[18626785]
AF464897: *Salmonella typhimurium* carboxymethyl-cellulase (celC) gene, complete cds
gi|18419673|gb|AF464897.1|[18419673]
AX339682: Sequence 3 from Patent WO0196382,
gi|18135684|emb|AX339682.1||pat|WO|0196382|3[18135684]
AX339680: Sequence 1 from Patent WO0196382,
gi|18135682|emb|AX339680.1||pat|WO|0196382|1[18135682]
AB063256: *Pseudomonas* sp. ND137 aclA gene for cellulase, complete cds,
gi|17826950|dbj|AB063256.1|[17826950]
AJ298117: *Ruminococcus flavefaciens* 17 endB gene for cellulase,
gi|16040919|emb|AJ298117.1|RFL298117[16040919]
AF033262: *Pseudomonas* sp. YD-15 endoglucanase gene, complete cds,
gi|4104165|gb|AF033262.1|AF033262[4104165]
AY039744: *Bacillus* sp. NBL420 cellulase (CelA) gene, complete cds,
gi|14994224|gb|AY039744.1|[14994224]
AJ315770: *Salmonella typhimurium* cellulose biosynthesis operon (bcsABZC),
gi|14626026|emb|AJ315770.1|STY315770[14626026]
AF289822: *Thermus caldophilus* cellulase (celA) gene, complete cds,
gi|14325793|gb|AF289822.1|AF289822[14325793]
AF355629: *Bacillus subtilis* Y106 alkali tolerable cellulase (cel) gene, complete cds,
gi|13785983|gb|AF355629.1|AF355629[13785983]
AB047845: *Clostridium thermocellum* celQ gene for endoglucanase Q, complete cds,
gi|13774110|dbj|AB047845.2|[13774110]
AF086819: *Thermobifida fusca* SbpA (sbpA) gene, partial cds; BglA (bglA), BglB (bglB),
BglC (bglC), and transcription regulator CelR (celR) genes, complete cds; and unknown
gene, gi|7160774|gb|AF086819.2|AF086819[7160774]
AY007311: *Clavibacter michiganensis* subsp. *sepedonicus* cellulase CelA gene, complete
cds, gi|13277512|gb|AY007311.1|[13277512]
AB018420: *Bacillus* sp. gene for cellulase, complete cds, isolate: KSM-S237,
gi|11874734|dbj|AB018420.1|[11874734]
AF132735: *Clostridium cellulovorans* endoglucanase K (engK), hydrophobic protein A
(hbpA), endoglucanase L (engL), mannanase A (manA), endoglucanase M (engM),
endoglucanase N (engN), and transposase (trp) genes, complete cds; and malate permease
(mln) gene, partial cds, gi|7363462|gb|AF132735.2|AF132735[7363462]
AY007248: *Fibrobacter succinogenes* S85 glycosyl hydrolase CelJ gene, partial cds; cellulase
Cel5K and xylanase Xyn10L genes, complete cds; and xylanase xyn10M gene, partial cds,
gi|9965983|gb|AY007248.1|[9965983]
AF233376: *Streptomyces* sp. 11AG8 cellulase 12A (cel12A) gene, complete cds,
gi|9651812|gb|AF233376.1|AF233376[9651812]
AF268074: *Thermomonospora fusca* cellulase precursor (Ex) gene, complete cds,
gi|8489860|gb|AF268074.1|AF268074[8489860]
AJ276358: *Erwinia rhapontici* celA gene for endoglucanase,
gi|7688165|emb|AJ276358.1|ERH276358[7688165]
M87018: *Clostridium cellulolyticum* cellulase gene cluster, complete sequence,
gi|5597001|gb|M87018.2|CLOCELCGE[5597001]
AF003696: *Cellvibrio mixtus* cellulase A (celA) gene, complete cds,
gi|2199544|gb|AF003696.1|AF003696[2199544]

TABLE 1-continued

Public nucleic acid accession numbers of useful enzymes

A79880: Sequence 1 from Patent WO9634108,
gi|6092776|emb|A79880.1||pat|WO|9634108|1[6092776]
A76937: Sequence 1 from Patent EP0739982,
gi|6088733|emb|A76937.1||pat|EP|0739982|1[6088733]
AF039030: *Clostridium thermocellum* cellulose 1,4-beta-cellobiosidase (celK) gene, complete cds, gi|2978565|gb|AF039030.1|AF039030[2978565]
AF103871: *Erwinia carotovora* subsp. *carotovora* transcription repressor (kdgR) gene, complete cds, gi|4926958|gb|AF103871.1|AF103871[4926958]
D16264: *Acetobacter xylinum* gene for CMCase, complete cds, gi|684951|dbj|D16264.1|ABCCMCASE[684951]
U72637: *Rhodothermus marinus* cellulase (celA) gene, complete cds, gi|2304960|gb|U72637.1|RMU72637[2304960]
AF130408: *Streptomyces viridosporus* strain T7A cellulase (celS1) mRNA, complete cds, gi|4583444|gb|AF130408.1|AF130408[4583444]
AB022867: *Prevotella ruminicola* genes for polyA polymerase, D-alanine glycinepermease and cellulase, complete cds, gi|4204221|dbj|AB022867.1|[4204221]
X04584: *Clostridium thermocellum* celD gene for endoglucanase D, gi|40671|emb|X04584.1|CTCELD[40671]
AB004098: *Bacillus* sp. KSM-522 gene for endo-1,4-beta-glucanase, complete cds, gi|2897801|dbj|AB004098.1|[2897801]
U05897: *Fibrobacter succinogenes* S85 endoglucanase E (celE) and endoglucanase D (celD) gene, complete cds, gi|1497855|gb|U05897.1|FSU05897[1497855]
U27084: *Bacillus* sp. bifunctional cellulase precursor (cel) gene, complete cds, gi|857575|gb|U27084.1|BSU27084[857575]
AF005277: *Cellulomonas biazotea* cellobiase (cba) gene, complete cds, gi|2921739|gb|AF005277.1|AF005277[2921739]
L39788: *Erwinia carotovora* subspecies *atroseptica* cellulase (CelN) gene, complete cds, gi|662360|gb|L39788.1|ERWCELN[662360]
L25809: *Cellulomonas fimi* cellulase, complete cds, gi|456028|gb|L25809.1|CFICELLASE[456028]
L02868: *Clostridium longisporum* endo-1,4-beta-D-glucanase (celA) gene, complete cds, gi|144754|gb|L02868.1|CLOCELAA[144754]
AB004845: *Clostridium josui* DNA for scaffolding protein, exoglucanase, complete cds, gi|3445476|dbj|AB004845.1|[3445476]
AB016164: *Bacillus* sp. gene for cellulase, complete cds, gi|3327376|dbj|AB016164.1|[3327376]
AB016163: *Bacillus* sp. gene for beta-mannanase, complete cds, gi|3327374|dbj|AB016163.11[3327374]
D00945: *Clostridium thermocellum* gene for endoglucanase, complete cds, gi|216412|dbj|D00945.1|CLOC307[216412]
AF067428: *Bacillus agaradhaerens* alkaline cellulase Cel5A (Cel5A) gene, complete cds, gi|3193119|gb|AF067428.1|AF067428[3193119]
AB006822: *Clostridium thermocellum* DNA for cellodextrin phosphorylase, complete cds, gi|2351100|dbj|AB006822.1|[2351100]
L01577: *Thermomonospora fusca* endo-1,4-beta-glucanase gene, complete cds, gi|3002467|gb|L01577.1|THFEBG[3002467]
D00066: *Bacillus* sp. gene for alkaline cellulase, complete cds, gi|216223|dbj|D00066.1|BAC139AC[216223]
AF045482: *Bacillus* sp. 79-23 endo-b-1,4-glucanase (celS) gene, complete cds, gi|2854063|gb|AF045482.1|AF045482[2854063]
AB008029: Thermophilic anaerobe NA10 gene for beta-glucanase, complete cds, gi|2564014|dbj|AB008029.1|[2564014]
U04629: *Streptomyces lividans* 66 cellulase B (celB) gene, complete cds, gi|2462717|gb|U04629.1|SLU04629[2462717]
Z86103: *T. neapolitana* celA and celB genes and two open reading frames, gi|1870178|emb|Z86103.1|TNZ86103[1870178]
E07931: DNA encoding *Bacillus* alkaline cellulase K-64, gi|2176063|dbj|E07931.1||pat|JP|1994217781|1[2176063]
E06128: DNA sequence of cellulase, gi|2174315|dbj|E06128.1||pat|JP|1993344884|1[2174315]
E03151: gDNA encoding cellulase, gi|2171368|dbj|E03151.1||pat|JP|1991240491|1[2171368]
E02652: gDNA encoding neutral cellulase, gi|2170880|dbj|E02652.1||pat|JP|1990265486|1[2170880]
E02571: DNA sequence encoding *Acetobacter xylinum* cellulase, gi|2170801|dbj|E02571.1||pat|JP|1990222688|1[2170801]
E02133: gDNA encoding alkaline cellulase, gi|2170371|dbj|E02133.1||pat|JP|1989281090|1[2170371]
E01477: Genomic DNA encoding alkaline cellase, gi|2169733|dbj|E01477.1||pat|JP|1987296874|2[2169733]
E01476: Genomic DNA encoding alkaline cellase, gi|2169732|dbj|E01476.1||pat|JP|1987296874|1[2169732]
E01354: Genomic DNA encoding cellulase, gi|2169611|dbj|E01354.1||pat|JP|1987232386|1[2169611]
E01258: DNA encoding cellulase, gi|2169517|dbj|E01258.1||pat|JP|1987175178|1[2169517]
D83704: *Clostridium thermocellum* DNA for endoglucanase, complete cds, gi|1663518|dbj|D83704.1|[1663518]
D16670: *Clostridium josui* celB gene for endo-1,4-beta-glucanase, complete cds, gi|391653|dbj|D16670.1|CLOCELB[391653]

TABLE 1-continued

Public nucleic acid accession numbers of useful enzymes

D01057: *B. subtilis* carboxymethyl cellulase (CMCase) gene,
gi|216387|dbj|D01057.1|BACCMCASE[216387]
U62023: *Erwinia carotovora* subsp. *carotovora* sensor/regulator protein RpfA (rpfA) gene,
complete cds, gi|2073555|gb|U62023.1|ECU62023[2073555]
Z33876: *Bacillus* sp. celB1 gene for endo-beta-1,4-glucanase,
gi|493468|emb|Z33876.1|BSCELB1[493468]
U30321: *Clostridium cellulolyticum* cellulosome integrating protein (CIPCCA) gene, partial cds, and cellulase precursor (celCCF) gene, complete cds,
gi|927290|gb|U30321.1|CCU30321[927290]
U04957: *Bacteroides ovatus* xylanase precursor gene and xylosidase/arabinosidase gene, complete cds, gi|450851|gb|U04957.1|B0U04957[450851]
A28170: *B. lautus* strain NCIM 40250 endocellulase gene 1 (Endo1),
gi|905293|emb|A28170.1||pat|WO19110732|1[905293]
X15208: *Serratia marcescens* chiB gene for chitinase B (EC 3.2.1.14),
gi|47227|emb|X15208.1|SMCHIB [47227]
X56082: *R. flavefaciens* DNA sequence of cellulase gene complex for endo-glucanase, exo-glucanase, beta-glucosidase and protease, gi|46152|emb|X56082.1|RFCGCP[46152]
Y00540: *Erwinia chrysanthemi* celZ gene for extracellular endoglucanase Z,
gi|141091|emb|Y00540.1|ECCE1Z[41091]
X88561: *F. succinogenes* cellulase gene, gi|887439|emb|X88561.1|FSCELLGEN[887439]
U12007: *Streptomyces lividans* 1326 ATP binding protein MsiK (msiK) gene, complete cds,
gi|607889|gb|U12007.1|SLU12007[607889]
L32742: *Caldocellum saccharolyticum* cellulase (celA) gene, complete cds
gi|537499|gb|L32742.1|CDCCELA[537499]
K03088: *Clostridium thermocellum* encoding endoglucanase A (celA) gene, complete cds,
gi|144752|gb|K03088.1|CLOCELA[144752]
M20921: *Streptomyces* sp. cellulase (cas A) gene, complete cds,
gi|153340|gb|M20921.1|STMLAS[153340]
L03218: *Streptomyces* sp. carboxymethylcellulase (casA) gene, complete cds,
gi|153201|gb|L03218.1|STMCASAA[153201]
L03800: *Ruminococcus flavefaciens* cellulase (celE) gene, complete cds,
gi|152634|gb|L03800.1|RUMCELE[152634]
L06942: *Clostridium thermocellum* cellulase Ss (celS) gene, complete cds,
gi|289858|gb|L06942.1|CLOCELSA[289858]
M58520: *F. succinogenes* ORF 1 and endo-1,4-beta-glucanase (FSendA) gene, complete cds and 3' end, gi|148572|gb|M58520.1|FIBFSENDA[148572]
M74044: *Erwina chrysanthemi* endoglucanase Y (celY) gene, complete cds,
gi|148391|gb|M74044.1|ERWCELY[148391]
M31903: *C. Thermocellum* cellulase (celH) protein genes, complete cds,
gi|144773|gb|M31903.1|CLOCELH[144773]
M36503: *C. uda* endoglucanase gene, complete cds,
gi|144430|gb|M36503.1|CFICMCASE[144430]
L02544: *Cellulomonas fimi* endo-1,4-beta-D-glucanase (cenD) gene, complete cds,
gi|144422|gb|L02544.1|CFICEND[144422]
M28332: *B. subtilis* cellulase gene, complete cds,
gi|142670|gb|M28332.1|BACCELD[142670]
M25500: *Bacillus* sp. endoglucanase (celC) gene, complete cds,
gi|142668|gb|M25500.1|BACCELC[142668]
M15743: *Bacillus* sp. cellulase gene, complete cds, clone pFK1,
gi|142666|gb|M15743.1|BACCELB [142666]
M27420: *Bacillus* sp. alkaline cellulase gene, complete cds,
gi|142664|gb|M27420.1|BACCELALKA[142664]
M14781: *Bacillus* sp. cellulase gene, complete cds, clone pNK1,
gi|142659|gb|M14781.1|BACCELA[142659]
M14729: *Bacillus* sp. cellulase gene, complete cds, clone pNK2,
gi|142655|gb|M14729.1|BACCEL[142655]
L04735: *Clostridium thermocellum* (clone RV 1.6) endo-1, 3-beta-glucanase (CMC) gene, complete cds, gi|144807|gb|L04735.1|CLOFEEGASE[144807]
L05368: *Ruminococccus flavefaciens* FD-1 beta-glucanase (celD) gene, complete cds,
gi|473844|gb|L05368.1|RUMCELDX[473844]
AY228551: *Actinobacillus actinomycetemcomitans* DspB (dspB) gene, partial cds
gi|30420959|gb|AY228551.1|[30420959]

In another embodiment, the invention provides a method for degrading biofilm produced by one or more bacterial strains wherein the method comprises contacting the biofilm with a cocktail comprising at least 2, 3, 4, 5, 6, 7, 8, 9, 10 or more different populations of phages, such as lambda phages, T7, T3, and T-even and T-even like phages, such as T2, T4 and RB69; also phages such as Pf1, Pf4, *Bacteroides fragilis* phage B40-8 and coliphage MS-2, wherein each phage population expresses on its surface at least one enzyme, preferably a biofilm matrix degrading enzyme. Such phage cocktails provide an efficient way to degrade biofilms, particularly biofilms that have been formed by multiple bacterial strains.

The phages in the cocktail may be from one or at least two different phage types. The type of biofilm affects the selection of the phages. For example, a dual biofilm comprising both *E. coli* and *P. aeruginosa*, would be best treated with at least one phage capable of infecting *E. coli*, such as T7 phage, and at least one phage capable of infecting *P. aeruginosa*, such as plaque forming phage Pf1 or Pf1-like Pf4 phage.

Particularly useful phages according to the invention are T7, T3 and *P. aeruginosa* bacteriophages, and genetically engineered combinations thereof, such as T7 phage that not only encodes a matrix degrading enzyme, but also encodes wild-type 10A and 10B capsid protein, to enhance the phage's replication in and lysis of, for example, *E. coli*. In one embodiment, the phage is T7 select 10-3b, encoding 10A capsid protein and a matrix degrading enzyme, such as cellulase, for example, cellulase A.

We have demonstrated that phages can be engineered to significantly reduce biofilm levels by simultaneously degrading the extracellular matrix and infecting biofilm-embedded cells. The multiplication of the engineered enzymatic phage during the subsequent lysis makes the biofilm reduction an efficient, autocatalytic process. These findings indicate that engineered enzymatic phages are useful for reducing and controlling biofilms in a variety of environmental, industrial and biotechnological settings. For example, such phages may prove useful in reducing biofilms that form in fermenters (12), water pipes and cooling towers (8), endoscopes (16), and dental unit water systems (17). In each of these cases, there is a practical need for novel, effective technologies for dispersing bacterial biofilms.

These enzymatic phages can also be used in conjunction with antibiotics to treat biofilm-related infections. Bacteriophages have been used for decades to treat human infections without standardized clinical trials (18), and there is an ongoing discussion about the benefits and hazards of employing phage as biopharmaceuticals (7, 18-21). While safety and efficacy issues, such as adverse immune response, release of endotoxins upon lysis, selection of phage-resistance strains, and the development of toxin-free phage preparations and effective non-replicating phage, remain as challenges, there are indications that these can be overcome (22-25). For example, phage have been engineered to kill bacterial cells without lysis in order to minimize toxin release (25).

As a technology to reduce and control biofilms, the engineered phage we have prepared offer a number of advantages over natural biofilm-degrading phage.

Firstly, only a small number of natural phages with biofilm-degrading activity have been identified and it is a significant challenge to isolate natural variants that exhibit a specific set of desirable characteristics (7). On the other hand, non-enzymatic natural phages have been isolated for a large number of biofilm-forming species and could be endowed with enzymatic, biofilm-degrading capabilities. This offers the potential for creating a suite of engineered enzymatic phage to target a variety of biofilm-forming species.

Secondly, the enzymatic activity of natural biofilm-degrading phage is highly specific (11,12). In contrast, engineered phage offer flexibility in the choice of enzymes that can be displayed on their surface and used to target and degrade a broad range of components in the extracellular matrix of biofilms. DNase I is one example of a biofilm-degrading enzyme (26) that provides an alternative to polysaccharide depolymerases and can be incorporated into enzymatic phage.

Thirdly, the phage-displayed enzymes utilized in engineered phages can be optimized for specific operating conditions, such as temperature and pH, using directed evolution methodologies (27). For example, our phage-borne cellulase only utilizes roughly 20% of its maximal activity at 37° C., indicating that its efficacy could be significantly improved.

Given the present knowledge of phage biology and the powerful genetic tools available, it is now possible to develop enzymatic phage to degrade different structural components in multi-species biofilms. This serves the purpose of reducing biofilm levels and/or making the biofilms more porous to increase the efficacy of other treatments, including disinfectants and antibiotics.

Accordingly, in one aspect, the invention provides a method of treating a surface with one or more phages expressing at least one biofilm degrading enzyme on their surface such that bacteria attached to the surface are killed or their growth is inhibited. In one embodiment, the surface is part of a device, e.g., a device that is used in medicine, e.g., surgical instruments, catheters and the like, agriculture, industrial processes, or water and wastewater treatment. In another embodiment, the surface is covered with a biofilm.

In another embodiment, the invention provides a method of degrading biofilm comprising contacting a surface infected with bacteria and/or comprising biofilm with at least one engineered phage, wherein the engineered phage expresses at least one biofilm-degrading enzyme on its surface.

In one embodiment, the invention provides a method of degrading biofilms formed by more than two bacteria. For example, one can target a dual-species biofilms, for example, biofilms formed by *E. coli* and *S. typhimurium*, or *E. coli* and *P. aeruginosa*.

In one embodiment, the invention provides a method of treating bacterial infection in a subject by providing the subject a phage that displays on its surface a biofilm degrading enzyme. In one embodiment, the method combines the use of phages with the use of antibiotic molecules.

Some phages have been engineered to be more efficient cloning vectors or naturally lack a gene important in infecting all bacteria, such as male and female bacteria in the biofilm. These phages would also often be most suitable for developing the engineered phages of the present invention. However, this engineering process may have adversely affected the capacity of the phage to replicate in naturally occurring bacteria thus limiting or preventing the use of these phages in degradation of biofilm produced by the naturally occurring bacteria.

For example, the capsid protein of phage T7, gene 10, comes in two forms, the major product 10A (36 kDa) and the minor product 10B (41 kDa) (Condron, B. G., Atkins, J. F., and Gesteland, R. F. 1991. Frameshifting in gene 10 of bacteriophage T7. J. Bacteriol. 173:6998-7003). Capsid protein 10B is produced by frameshifting near the end of the coding region of 10A. NOVAGEN® modified gene 10 in T7 to remove the frameshifting site so that only 10B with the attached user-introduced peptide for surface display is produced (U.S. Pat. No. 5,766,905. 1998. Cytoplasmic bacteriophage display system). The 10B-enzyme fusion product is too large to make up the entire phage capsid because the enzymes that are typically introduced into phages, such as T7, are large (greater than a few hundred amino acids). As a result, T7select 10-3b must be grown in host bacterial strains that produce wild-type 10A capsid protein, such as BLT5403 or BLT5615, so that enough 10A is available to be interspersed with the 10B-enzyme fusion product to allow replication of phage (U.S. Pat. No. 5,766,905. 1998. Cytoplasmic bacteriophage display system). However, because most biofilm-forming *E. coli* do not produce wild-type 10A capsid protein, this limits the ability of T7select 10-3b displaying large enzymes on their surface to propagate within and lyse some important strains of *E. coli*.

Accordingly, the invention provides genetically engineered phages that in addition to displaying a biofilm degrading enzyme on their surface, also express all the essential genes for virus replication in naturally occurring bacterial strains. In one embodiment, the invention provides an engineered T7select 10-3b phage that expresses both cellulase and 10A capsid protein.

It is known that wild-type T7 does not productively infect male (F plasmid-containing) *E. coli* because of interactions between the F plasmid protein PifA and T7 genes 1.2 or 10 (Garcia, L. R., and Molineux, I. J. 1995. Incomplete entry of bacteriophage T7 DNA into F plasmid-containing *Escherichia coli*. J. Bacteriol. 177:4077-4083.). F plasmid-containing *E. coli* infected by T7 die but do not lyse or release large numbers of T7 (Garcia, L. R., and Molineux, I. J. 1995. Incomplete entry of bacteriophage T7 DNA into F plasmid-containing *Escherichia coli*. J. Bacteriol. 177:4077-4083). Wild-type T3 grows normally on male cells because of T3's gene 1.2 product (Garcia, L. R., and Molineux, I. J. 1995, Id.). When T3 gene 1.2 is expressed in wild-type T7, T7 is able to productively infect male cells (Garcia, L. R., and Molineux, I. J. 1995. Id).

Because many biofilm-producing *E. coli* contain the F plasmid (Ghigo, J. M. 2001. Natural conjugative plasmids induce bacterial biofilm development. Nature. 412:442-445), it is important, although not necessary, for an engineered phage to be able to productively infect also male cells. Therefore, in addition to engineering the phage to display a biofilm degrading enzyme on its surface, one can also engineer it to express the gene necessary for infecting the male bacteria. For example, one can use the modification described by Garcia and Molineux (Garcia, L. R., and Molineux, I. J. 1995. Incomplete entry of bacteriophage T7 DNA into F plasmid-containing *Escherichia coli*. J. Bacteriol. 177:4077-4083) to express T3 gene 1.2 in T7.

The references cited herein and throughout the specification are herein incorporated by reference in their entirety.

REFERENCES

1. Costerton J. W., Stewart P. S. and Greenberg E. P. Science 284, 1318-1322 (1999).
2. Davey M. E. and O'Toole G. A. Microbiol. Mol. Biol. Rev. 64, 847-867 (2000).
3. Hall-Stoodley L., Costerton J. W. and Stoodley P. Nat. Rev. Microbiol. 2, 95-108 (2004).
4. Mah T.-F. C. and O'Toole G. A. Trends Microbiol. 9, 34-39 (2001).
5. Hogan D. and Kolter R. Curr. Opin. Microbiol. 5, 472-477 (2002).
6. Stewart P. S. and Costerton J. W. Lancet 358, 135-138 (2001).
7. Projan S, Nat. Biotechnol. 22, 506-507 (2004).
8. Doolittle M. M., Cooney J. J. and Caldwell D. E. Can. J. Microbiol. 41, 12-18 (1995).
9. Doolittle M. M., Cooney J. J. and Caldwell D. E. J. Ind. Microbiol. 16, 331-341 (1996).
10. Corbin B. D., McLean R. J. and Aron G. M. Can. J. Microbiol. 47, 680-684 (2001).
11. Sutherland I. W., Hughes K. A., Skillman L. C. and Tait K. FEMS Microbiol. Lett. 232, 1-6 (2004).
12. Hughes K. A., Sutherland I. W. and Jones M. V. Microbiology 144, 3039-3047 (1998).
13. Danese P. N., Pratt L. A. and Kolter R. J. Bacteriol. 182, 3593-3596 (2000).
14. Zogaj X., Nimtz M., Rohde M., Bokranz W. and Romling U. Mol. Microbiol. 39, 1452-1463 (2001).
15. O'Toole G. A. and Kolter R. Mol. Microbiol. 28, 449-461 (1998).
16. Vickery K., Pajkos A. and Cossart Y. Am. J. Infect. Control 32, 170-176 (2004).
17. Walker J. T., Bradshaw D. J., Fulford M. R., Martin M. V. and Marsh P. D. In: Biofilm Community Interactions: Chance or Necessity? (Eds. Gilbert P., Allison D., Brading M., Verran J. and Walker J.) Bioline (Cardiff, UK), 333-340 (2001).
18. Merril C. R, Scholl D. and Adhya S. L. Nat. Rev. Drug Discov. 2, 489-497 (2003).
19. Thiel K. Nat. Biotechnol. 22, 31-36 (2004).
20. Projan S. Nat. Biotechnol. 22, 167-168 (2004).
21. Schoolnik G. K., Summers W. C. and Watson J. D. Nat. Biotechnol. 22, 505-506 (2004).
22. March J. B., Clark J. R. and Jepson G. D. Vaccine 22, 1666-1671 (2004).
23. Matsuzaki S. et al. J. Infect. Dis. 187, 613-624 (2003).
24. Boratynski J., Syper D., Weber-Dabrowska B., Lusiak-Szelachowska M., Pozniak G. and Gorski A. Cell. Mol. Biol. Lett. 9, 253-259 (2003).
25. Hagens S, and Blasi U. Lett. Appl. Microbiol. 37, 318-323 (2003).
26. Whitchurch C. B., Tolker-Nielsen T., Ragas P. C. and Mattick J. S. Science 295, 1487 (2002).
27. Fernandez-Gacio A., Uguen M., and Fastrez J. Trends Biotechnol. 21, 408-414 (2003).

EXAMPLE 1

Preparation of Enzymatically Active Bacteriophage: We have engineered enzymatically active bacteriophage that significantly reduce *Escherichia coli* biofilm by simultaneously degrading the extracellular biofilm matrix, and infecting and lysing biofilm-embedded cells.

Bacteria typically grow in surface-attached communities known as biofilms, which consist of cells encased in an extracellular matrix (1-3). Biofilms form on the surfaces of a variety of environmental, industrial, and biological systems, including water distribution systems, fermenters and medical devices. Because biofilm-encased cells have increased resistance to antibiotics and disinfectants, they are sources of contamination that are difficult to eliminate (4,5). There is a clear and growing need for novel technologies to reduce and control biofilms (6). To address this need, we have engineered enzymatically active bacteriophage to disperse mature biofilm, for example formed by *Escherichia coli*.

Bacteriophages are bacteria-specific viruses that propagate by hijacking the host's replication and synthesis machinery, and releasing phage progeny by cell lysis. The encasing of bacterial cells in a biofilm may provide protection against phage infection, and this has been advanced as a serious obstacle for the development of phage-based therapeutics (7). However, phage T4 is able to infect and multiply within *E. coli* biofilms (8-10), and some phage exhibit enzymatic activity that can degrade the extracellular biofilm matrix (11). For example, phage-SF153b break down surface-attached Enterobactor agglomerans communities by combining enzymatic matrix digestion and cell lysis (12). The enzymatic phage employed in this study are engineered to disperse biofilms following a similar two-pronged strategy (FIG. 1): (1) the enzymatic activity of the phage degrades the extracellular matrix of the biofilm, thus exposing the biofilm-embedded cells, and (2) the phage infect and lyse the exposed cells, releasing additional enzymatic phage in the process.

Figure 2:
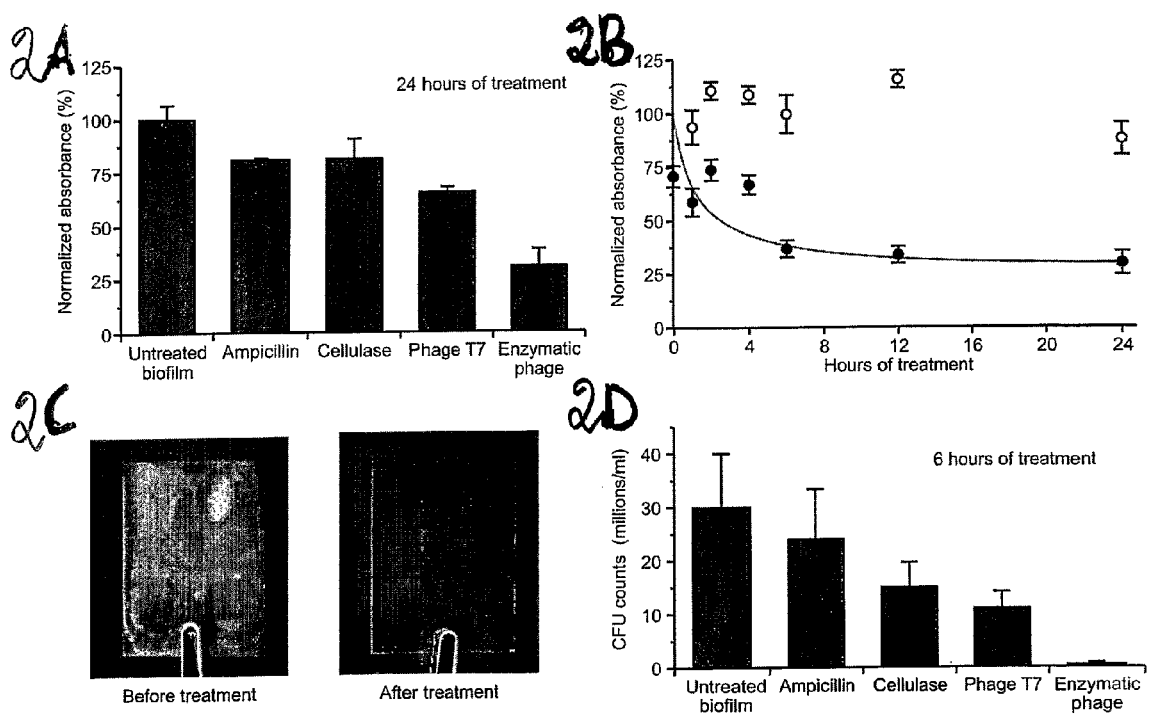
FIGS. 2A-2D show treatment of mature *E. coli* biofilm.

The extracellular matrix of bacterial biofilms contains a variety of polysaccharides. For example, colanic acid has been identified in *E. coli* biofilms (13), and cellulose has been reported to be a component of dual-species biofilms formed by *E. coli* and *Salmonella typhimurium* (14). We confirmed the presence of extracellular cellulose in *E. coli* colonies using a Congo-red assay. To identify cellulose as a structural component of the extracellular biofilm matrix, we treated mature *E. coli* biofilms formed in the wells of a microtiter plate with purified cellulase. This led to a dose-dependent reduction in biofilm levels, as quantified by a crystal violet (CV) microtiter absorbance assay (15). As shown in FIG. 2A, treatment with purified cellulase (20 units/ml for 24 hours at 37° C.) led to a reduction in biofilm levels similar to that observed with ampicillin (100 μg/ml) and phage T7 (2.4×10⁸ particles/ml) treatment, respectively.

To combine the effects of phage-induced lysis and cellulase-induced biofilm degradation, we modified the genome of phage T7 such that the enzyme cellulase A, encoded by the celA gene from *Clostridium thermocellum*, is displayed on the surface of the phage. The cellulase activity of this enzymatic phage was measured to be approximately 0.6 units/10¹⁰ particles (see Supplemental Information). As can be seen in FIG. 2A, treatment of mature biofilm with enzymatic phage (2.2×10⁸ particles/ml) resulted in a significantly greater reduction in biofilm levels than treatment with either purified cellulase or phage T7. These comparisons are surprising, given that the enzymatic activity of the engineered phage (0.012 units/ml) was over a thousand-fold less than that of the purified cellulase. In addition, measurements of CV staining after different periods of treatment suggest that the enzymatic phage treatment exerts its effect in approximately 6 hours (FIG. 2B).

Based on the absorbance value of a sterile well (negative control), the CV staining-measurements-presented in FIGS. 2A and 2B suggest that the reduction in biofilm level by the enzymatic phage is about 70%. However, the absorbance measured after enzymatic phage treatment is similar to that measured when wells are incubated with strains known to be defective in biofilm formation. This shows that the efficacy of the enzymatic phage is likely even greater than that indicated by the CV staining assay.

To further explore the efficacy of the enzymatic phage, we employed two additional methods to evaluate biofilm levels. In FIG. 2C, we show the effect of enzymatic phage treatment on a mature biofilm grown on a glass plate immersed in a microfermenter. A significant reduction in biofilm levels is evident by comparison of digital photographs taken before and after 6-hour treatment with the enzymatic phage. As a second quantitative measure, we determined the number of viable cells by counting colony-forming units (CFU) after 6 hours of treatment with the same conditions as in FIG. 2A. The CFU counts (FIG. 2D) confirm both the result from the CV staining assay (FIG. 2A), that enzymatic phage perform significantly better than the other treatments, and the finding from the microfermenter experiment (FIG. 2C), that enzymatic phage treatment leads to a significant reduction in biofilm levels.

Strains, phage, plasmid, genes and chemicals: Wild type bacteriophage T7 and the genome of *Clostridium thermocellum* were obtained from ATCC (Manassas, Va.). All chemicals, including ampicillin, kanamycin, crystal violet, Congo-red and cellulase (from Asperugillus niger) were obtained from Sigma (St. Louis, Mo.). *E. coli* strains were obtained from CGSC (New Haven, Conn.). The strain HK1 (lacI::Kan) used in the biofilm experiments was obtained from wild type strain K-12 (CGSC#: 7296) by one-step inactivation (Datsenko K. A. and Wanner B. L. Proc. Natl. Acad. Sci. USA 97, 6640-6645 (2000)) of laI. A similarly obtained strain HK2 (laa:Kan, F'traA::Cm) and strain 2.300 (CGSC#: 5002) were used in control experiments for the crystal violet staining assay (presented below). Both strains are unable to form biofilm (Ghigo J.-M. Nature 412, 442-445 (2001)). *E. coli* strains BLT5403 and BLT5615 were used to isolate wild type and recombinant phage T7.

Phage display: The enzymatic phage were engineered using the T7Select System (Novagen Inc., Darmstadt, Germany). The celA gene from *C. thermocellum* was isolated by PCR using the primers 5'-catg aat tcT GCA GGT GTG CCT TTT AAC ACA AAA TAC-3' (SEQ ID NO:1) and 5'-gac-gtc aag.ctt TTT CCG TAA ATC TGT CAA AAA CCC ATT ACA-3' (SEQ ID NO: 2), and cloned into the T7 genome via EcoRI and HindIII sites. Insertion was confirmed by sequencing. After in vitro packaging, phage particles were obtained and isolated from liquid lysate by centrifugation (150,000×g for 90 minutes at 4° C.). The concentration of stock solutions of phage T7 and enzymatic phage was determined as follows. 100 μl diluted stock solutions and 200 μl of an overnight *E. coli* culture were added to 4 ml warm (about 42° C.) LB broth containing 0.6% w/v agar. The solution was mixed and poured onto a hardened LB-agar plate and incubated at room temperature for 8-12 hours before counting of phage plaques. Phage particles carrying a control insert (S.tag peptide, 15 amino acids) were used to confirm that the recombinant phage in the T7Select system have no detectable effect on the dispersion of the biofilm compared to wild type phage T7.

Figure 3:
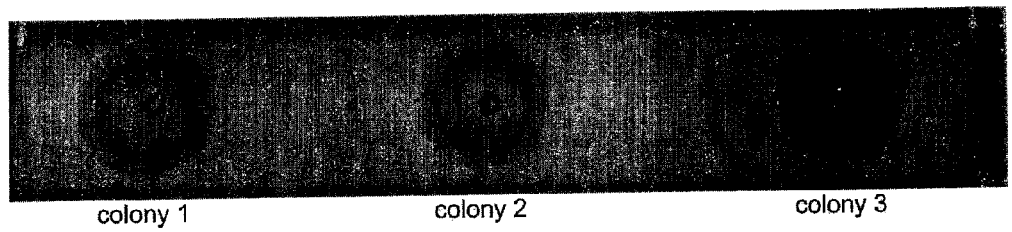
FIG. 3 shows photographs of three *E. coli* strain K-12 colonies grown on LB agar plates containing Congo-red.

Congo-red assay: To identify cellulose as a potential target of an engineered enzymatic phage, wild-type *E. coli* strain K-12 was inoculated onto an LB Agar plate containing 40 μg/ml Congo-red as described in Hammar M., Arnqvist A., Bian Z., Olsen A. and Normark S. Mol. Microbiol. 18, 661-670 (1995). The formation of a red ring (FIG. 3) indicates the presence of extracellular cellulose.

Figure 4:
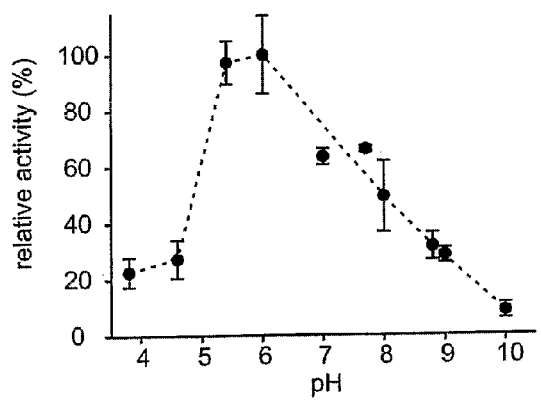
FIGS. 4A-4B show enzymatic activity of the enzymatic phage at different pH (FIG. 4A) and temperature (FIG. 4B).
Figure 4:
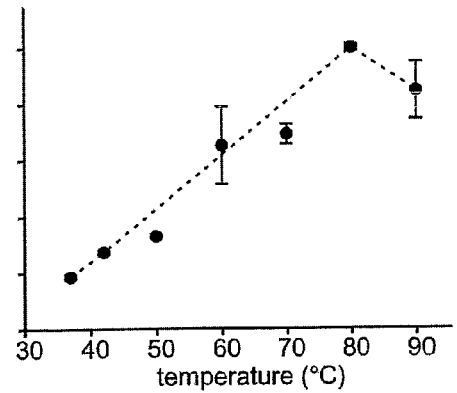

Cellulase activity measurements: Phage solution was mixed with 1% azo-CM-cellulose (Megazyme, Wicklow, Ireland) in a 50 mM sodium phosphate buffer (pH 7.0) and incubated at 37° C. for 2-3 hours. Undigested azo-CM-cellulose was precipitated with a solution of 0.5 M sodium acetate, 3.6 mM zinc acetate and 80% ethanol, and removed by centrifugation (1,000×g for 10 minutes). The absorbance of the supernatant was measured at 590 nm using a Hitachi U-3000 spectrophotometer. *A. niger* cellulase was used as a standard for the calculation of activity units. The cellulase activity of the modified phage was measured to be 0.56±0.02 units/10¹⁰ particles (n=3) at 37° C. and pH 7. The effect of varying pH and temperature on the enzymatic activity of the engineered phage is shown in FIGS. 4A and 4B. The phage have optimal catalytic activity at pH 6 and 80° C., with approximately 20% activity retained at pH 7 and 37° C.

Biofilm maturation and treatment: All experiments were performed using M63 minimal medium (1.052 g/l $KH_2PO_4$, 5.613 g/l $K_2HPO_4$, 2.0 g/l $(NH_4)_2SO_4$, 0.50 mg $FeSO_4(H_2O)_7$, 1.0 mmol $MgSO_4$, pH 7.2), supplemented with 0.4% w/v glucose and kanamycin as the selective marker. Microtiter assays emplyed three different types of 96-well polystyrene microtiter plates. The staining experiments in FIG. 2A employed BD Biosciences Falcon brand microplates (catalogue number 353228). The staining and viable cell count experiments in FIGS. 2B and 2D, respectively, employed Nunc-Immuno BreakApart microplates (catalogues number 473768). The latter were heat-treated at 60° C. for seven days before being used in the experiments.

To cultivate biofilm in microplates, wells containing 100 μl medium were inoculated with 100-fold diluted overnight cultures followed by growth in a TECAN SpectraFluor Plus instrument for 48 hours at 37° C. with continuous shaking. The liquid phase was carefully replaced with 100 μl fresh medium at intervals of 12 hours to ensure development of a thick mature biofilm. After 48 hours of cultivation, the liquid phase was replaced with 100 μl fresh medium supplemented with sterile water, ampicillin, cellulase, bacteriophage T7 particles, or enzymatic phage particles, and incubated for up to 24 hours (crystal violet staining experiments; FIGS. 2A and 2B) or 6 hours (viable cell count experiments; FIG. 2C).

In the microfermenter experiments, flow reactors with three injector ports were constructed to obtain a flow rate of approximately 13 ml/hour and a culture volume of approximately 20 ml. Corning glass plates were submerged as the substratum for the biofilm. Experiments were started by inoculating 20 ml fresh medium with 200 μl 1:100 dilutions of overnight cultures followed by incubation in a water bath at 37° C. and constant stirring provided by sterile aeration. After 48 hours of cultivation, the glass plate was briefly extracted, rinsed with sterile water and a digital photograph was taken. A single dose of enzymatic phage particles was injected into the microfermenter, and the glass plate was incubated for 1 hour in the microfermenter with no flow, followed by cultivation at a flow rate of 13 ml/hour. After a total of 6 hours of treatment, the glass plate was extracted from the microfermenter and a digital photograph was taken (FIG. 2C).

Crystal violet staining: We followed protocols described in O'Toole G. A. and Kolter R. Mol. Microbiol. 28, 449-461 (1998); and Jackson D. W., Suzuki K., Oakford L., Simecka J. W., Hart M. E. and Romeo T. J. Bacteriol. 184, 290-301 (2002)). After the appropriate incubation period; the liquid culture phase was removed from the wells and discarded, and the material remaining in the wells was washed three times with 300 μl medium. After the initial wash, 100 μl of a 1% crystal violet solution was added to each well, incubated for 15 minutes at room temperature, and washed three times with double-distilled water. 100 μl 33% acetic acid was subsequently added to solubilize the dye (Jackson D. W., Suzuki K., Oakford L., Simecka J. W., Hart M. E. and Romeo T. J. Bacteriol. 184, 290-301 (2002)) and the wells were inoculated for 15 minutes before being assayed at 600 nm using a TECAN SpectraFluor Plus plate reader.

The CV staining assay was found to yield moderately high absorbance values not only after enzymatic phage treatment (FIGS. 2A and 2B), but also when the wells were inoculated with strains HK2 and 2.300 that do not form biofilm (Ghigo J.-M. Nature 412, 442-445 (2001)). For the Nunc brand plate (FIG. 2B), the absorbance measured after 72 hours (48 hours of maturation plus 24 hours of treatment) was 2.6 for wells inoculated with strain HK1 (mature biofilm), 0.88 for wells inoculated with strain HK2, 0.83 for wells inoculated with strain 2.300, and 0.20 for wells containing media only. The Fisher brand plates used in FIG. 2A consistently yielded an absorbance of approximately 25% of that measured from the Nunc brand plates. The moderately high absorbance values measured for the non-biofilm forming strains and after enzymatic phage treatment, which are about 25-30% of that measured for wells containing mature biofilm, may arise from sedimentation of cells at the liquid-air boundary. Such sediments were detectable visually in all of the microplate experiments.

Viable cell counts: To determine the number of colony forming units (CFU), the liquid culture phase was carefully removed from each well, and the wells were washed three times with 300 μl fresh medium. After the wash, 200 μl fresh medium was added to each well and the well walls were carefully scraped to suspend sediments in the liquid phase. Individual wells were subsequently separated from the microplate and placed in a test tube containing 1.8 ml fresh medium (total volume of 2 ml). The test tubes were sonicated for 7 minutes at 40 kHz in a sonic water bath (Branson Ultrasonics model 2210). To determine CFU counts, three 100 μl cell suspensions were extracted from each test tube and spread onto LB agar plates in triplicates (nine plates per test tube) after appropriate dilution. Colonies were counted after overnight incubation at 37° C.

EXAMPLE 2

Engineering T7select 10-3b to Produce Wild-Type 10A: We chose Novagen T7select 10-3b as the starting bacteriophage for the engineered phage. The capsid protein of T7, gene 10, comes in two forms, the major product 10A (36 kDa) and the minor product 10B (41 kDa) (1). Capsid protein 10B is produced by frameshifting near the end of the coding region of 10A. Novagen modified gene 10 in T7 to remove the frameshifting site so that only 10B with the attached user-introduced peptide for surface display is produced (2). The 10B-enzyme fusion product is too large to make up the entire phage capsid because the enzymes that are typically introduced into phages, such as T7, are large (greater than a few hundred amino acids). As a result, T7select 10-3b must be grown in host bacterial strains that produce wild-type 10A capsid protein, such as BLT5403 or BLT5615, so that enough 10A is available to be interspersed with the 10B enzyme fusion product to allow replication of phage (2). However, because most biofilm-forming E. coli do not produce wild-type 10A capsid protein, this limits the ability of T7select 10-3b displaying large enzymes on their surface to propagate within and lyse some important strains of E. coli.

As a result, we engineered T7select 10-3b, in addition to producing a biofilm degrading cellulase enzyme, to also produce enough wild-type 10A capsid protein to allow it to replicate in hosts that do not produce 10A.

T7select 10-3b comes as a cloning kit with two vector arms into which users can insert genes. The left vector arm has an EcoRI site, where the 5' end of the insert should be, while the right vector arm has a HindIII site, where the 3' end of the insert should be. Therefore, all designs described here contain an EcoRI site at the 5' end and a HindIII site at the 3' end.

Construct I: EcoRI-BsiWI-SexAI-φ10-s10-10A-HindIII: Our initial design was to simply copy the 10A gene with its φ10 promoter and s10 ribosome binding site (RBS) in the pAR5403 plasmid in the BLT5403 host and insert this into T7select 10-3b. pAR5403 contains the φ10 promoter, the s10 RBS, and a modified 10A gene. pAR5403 was isolated from BLT5403 via the QIAgen QIAprep kit. In order to copy φ10-s10-10A, we built a sequence containing an EcoRI site at the 5' end, followed by a BsiWI site, followed by stop codons in all three reading frames, followed by a SexAI site, followed by stop codons in all three reading frames, followed by φ10, s10, and 10A from pAR5403 followed by a HindIII site at the 3' end.

We used overlapping PCR primers to build the EcoRI-BsiWI-SexAI sequence that was 5' to the φ10-s10-10A gene. The sequences for the 5' end primers were (in order of application):

| Name | Sequence | SEQ ID No: |
|---|---|---|
| a-10Aphi10s10 | 5' gTA AcT AA cgaaattaat acgactcact atagg 3' | 3 |
| b-10Aphi10s10 | 5' C CTG GTc TAA gTA AcT AA cgaaattaat acgactc 3' | 4 |
| c-10Aphi10s10 | 5' c TAA gTA AcT AAC CTG GTc TAA gTA AcT AA cgaa 3' | 5 |

| Name | Sequence | SEQ ID No: |
|---|---|---|
| d-10Aphi10s10 | 5' gt gtC GTA CGc TAA gTA AcT AAC CTG GTc TAA gT 3' | 6 |
| e-10Aphi10s10 | 5' gcat G AAT TCa ggt gtC GTA CGc TAA gTA AcT A 3' | 7 |

We used several 3' end primers to introduce the HindIII site depending on melting temperatures needed to match the 5' primer:

| Name | Sequence | SEQ ID NO: |
|---|---|---|
| 10A-rev-med | 5' ctgc AAGCTT TTATTCCACTTTAA AG 3' | 8 |
| 10A-rev-short | 5' ctgc AAGCTT TTATTCCACTTTA 3' | 9 |
| 10A-rev-long | 5' ctgc AAGCTT TTATTCCACTTTAA AGACCAC 3' | 10 |
| 10A-rev-longer | 5' ctgc AAGCTT TTATTCCACTTTAA AGACCACTGC 3' | 11 |

The final expected sequence from the PCR reaction is for EcoRI-BsiWI-SexAI-φ10-s10-10A-HindIII is (1186 bp):

5' gcat GAATTC aggtgt CGTACG cTAAgTAAcT AA CCTGGT cTAAgTAAcT AA cgaaattaat acgactcact atagg-gagac cacaacggtt tccctctaga aataattttg tttaacttta agaaggagat atacatatgg ctagcatgac tggtggacag caaatgggta ctaaccaagg taaaggtgta gttgctgctg gagataaact ggcgttgttc ttgaaggtat ttggcg-gtga agtcctgact gcgttcgctc gtacctccgt gaccacttct cgccacatgg tacgttccat ctccagcggt aaatccgctc agttccctgt tctgggtcgc actcag-gcag cgtatctggc tccgggcgag aacctcgacg ataaacgtaa ggacat-caaa cacaccgaga aggtaatcac cattgacggt ctcctgacgg ctgacgttct gatttatgat attgaggacg cgatgaacca ctacgacgtt cgctctgagt atac-ctctca gttgggtgaa tctctggcga tggctgcgga tggtgcggtt ctggct-gaga ttgccggtct gtgtaacgtg gaaagcaaat ataatgagaa catcgagggc ttaggtactg ctaccgtaat tgagaccact cagaacaagg ccgcacttac cgac-caagtt gcgctgggta aggagattat tgcggctctg actaaggctc gtgcg-gctct gaccaagaac tatgttccgg ctgctgaccg tgtgttctac tgtgacccag atagctactc tgcgattctg gcagcactga tgccgaacgc agcaaactac gct-gctctga ttgaccctga gaagggttct atccgcaacg ttatgggctt tgaggttgta gaagttccgc acctcaccgc tggtggtgct ggtaccgctc gtgagggcac tactggtcag aagcacgtct tccctgccaa taaaggtgag ggtaatgtca aggt-tgctaa ggacaacgtt atcggcctgt tcatgcaccg ctctgcggta ggtactgtta agctgcgtga cttggctctg gagcgcgctc gccgtgctaa cttccaagcg gac-cagatta tcgctaagta cgcaatgggc cacggtggtc ttcgcccaga ag CTGCTGGT GCAGTGGTCT TTAAAGTGGA ATAA AAGCTT gcag 3' (SEQ ID NO: 12)

The cloned insert containing the cellulase gene can be ligated to the EcoRI-BsiWI-SexAI-φ10-s10-10A-Hind III product at the BsiWI or SexAI sites.

Construct II: EcoRI-BsiWI-SexAI-s10-10A-HindIII: We also designed a construct with the φ10 promoter removed because we were not sure how much 10A should be produced relative to the 10B-enzyme fusion product to ensure proper assembly of the phage capsid while maintaining adequate expression of the 10B-enzyme fusion product on the surface of the phage.

We copied the 10A gene with its s10 RBS from the pAR5403 plasmid in the BLT5403 host and inserted this into T7select 10-3b. pAR5403 contains the φ10 promoter, the s10 RBS, and a modified 10A gene. pAR5403 was isolated from BLT5403 via the QIAgen QIAprep kit: hi order to copy s10-10A, we built a sequence containing an EcoRI site at the 5' end, followed by a BsiWI site, followed by stop codons in all three reading frames, followed by a SexAI site followed by stop codons in all three reading frames, followed by s10 and 10A from pAR5403, followed by a HindIII site at the 3' end.

We used overlapping PCR primers to build the EcoRI-BsiWI-SexAI sequence that was 5' to the s10-10A gene. The sequences for the 5' end primers were (in order of application):

| Name | Sequence | SEQ ID No: |
|---|---|---|
| a-10As10 | 5' cT AA aataattttg tttaacttta agaaggagat 3' | 13 |
| b-10As10 | 5' gTA AcT AA aataattttg tttaacttta agaagg 3' | 14 |
| c-10As10 | 5' GTc TAA gTA AcT AA aataattttg tttaacttta ag 3' | 15 |
| d-10As10 | 5' AC CTG GTc TAA gTA AcT AA aataattttg tttaact 3' | 16 |
| e-10As10 | 5' c TAA gTA AcT AAC CTG GTc TAA gTA AcT AA aataat 3' | 17 |
| d-10Aphi10s10 (same as above) | 5' gt gtC GTA CGc TAA gTA AcT AAC CTG GTc TAA gT 3' | 18 |
| e-10Aphi10s10 (same as above) | 5' gcat G AAT TCa ggt gtC GTA CGc TAA gTA AcT A 3' | 19 |

We used several 3' end primers to introduce the HindIII site depending on melting temperatures needed to match the 5' primer:

| Name | Sequence | SEQ ID NO: |
|---|---|---|
| 10A-rev-med | 5' ctgc AAGCTT TTATTCCACTTTAA AG 3' | 20 |
| 10A-rev-short | 5' ctgc AAGCTT TTATTCCACTTTA 3' | 21 |
| 10A-rev-long | 5' ctgc AAGCTT TTATTCCACTTTAA AGACCAC 3' | 22 |
| 10A-rev-longer | 5' ctgc AAGCTT TTATTCCACTTTAA AGACCACTGC 3' | 23 |

The final expected sequence from the PCR reaction is for EcoRI-BsiWI-SexAI-s10-10A-HindIII is (1136 bp):

5' gcat GAATTC aggtgt CGTACG cTAAgTAAcTAA CCTGGT cTAAgTAAcTAA aataattttg tttaacttta agaaggagat atacatatgg ctagcatgac tggtggacag caaatgggta ctaaccaagg taaaggtgta gttgctgctg gagataaact ggcgttgttc ttgaaggtat ttggcggtga agtcctgact gcgttcgctc gtacctccgt gaccacttct cgccacatgg tacgttccat ctccagcggt aaatccgctc agttccctgt tctgggtcgc actcaggcag cgtatctggc tccgggcgag aacctcgacg ataaacgtaa ggacatcaaa cacaccgaga aggtaatcac cattgacggt ctcctgacgg ctgacgttct gatttatgat attgaggacg cgatgaacca ctacgacgtt cgctctgagt atacctctca gttgggtgaa tctctggcga tggctgcgga tggtgcggtt ctggctgaga ttgccggtct gtgtaacgtg gaaagcaaat ataatgagaa catcgagggc ttaggtactg ctaccgtaat tgagaccact cagaacaagg ccgcacttac cgaccaagtt gcgctgggta aggagattat tgccggctctg actaaggctc gtgcggctct gaccaagaac tatgttccgg ctgctgaccg tgtgttctac tgtgacccag atagctactc tgccgattctg gcagcactga tgccgaacgc agcaaactac gctgctctga ttgaccctga gaagggttct atccgcaacg ttatgggctt tgaggttgta gaagttccgc acctcaccgc tggtggtgct ggtaccgctc gtgagggcac tactggtcag aagcacgtct tccctgccaa taaaggtgag ggtaatgtca aggttgctaa ggacaacgtt atcggcctgt tcatgcaccg ctctgcggta ggtactgtta agctgcgtga cttggctctg gagcgcgctc gccgtgctaa cttccaagcg gaccagatta tcgctaagta cgcaatgggc cacggtggtc ttcgcccaga ag CTGCTGGT GCAGTGGTCT TTAAAGTGGA ATAA AAGCTT gcag 3' (SEQ ID NO: 24).

The cloned insert containing the cellulase gene can be ligated to the EcoRI-BsiWI-SexAI-s10-10A-HindIII product at the BsiWI or SexAI sites.

Construct III: EcoRI-BsiWI-SexAI-φ10-s10-10A-HindIII with Modified Ribosome Binding Sites: Because we were unsure whether the φ10-s10-10A gene copied from pAR5403 was going to produce too much or too little 10A when inserted into T7select 10-3b, we decided to mutate existing ribosome binding sites within s10. Since pAR5403 is a high-copy plasmid and we were inserting only one copy of the φ10-s10-10A gene in construct one, we decided to try to increase the strength of the RBS by using a more complete Shine-Delgarno (SD) sequence or modifying the aligned spacing, which is defined as the distance between the end of a full-length 9 base pair SD sequence and the 10A translation start codon or if the SD sequence is shorter, the distance between where the end of the complete SD would be and the 10A translation start codon. The actual spacing between the SD sequence and the 10A translation start codon is the same as the aligned spacing if the SD is 9 nucleotides long but may be different if the SD is not 9 nucleotides.

There is an XbaI site within Construct I (EcoRI-BsiWI-SexAI-φ10-s10-10A-HindIII) shown in bold font in the Construct I sequence above. We amplified the 10A gene itself and build out new Shine-Delgarno sequences using overlapping primers in sequential PCR reactions up to the XbaI site. These products can then be ligated to the 5' piece of Construct I cut at the XbaI site (highlighted in yellow in the Construct I sequence above) to create a new EcoRI-BsiWI-SexAI-φ10-s10-10A-HindIII construct with a modified RBS within s10.

We designed four different SD sequences. SD#1 has the full SD sequence (5' TAAGGAGGT 3', SEQ ID NO: 25) and an aligned spacing of 5 nucleotides (5' ATAAT 3'). SD#2 has the full SD sequence (5' TAAGGAGGT 3') (SEQ ID NO: 25) and an aligned spacing of 5 nucleotides different from those in SD#1 (5' AGAAT 3'). SD#3 has the same SD in the wild-type s10 RBS. (5' AAGGAG 3') with an aligned spacing of 5 nucleotides (an actual spacing of 7 nucleotides because the SD only encompasses nucleotides 2 to 7, inclusive, of the full-SD) (5' AAAGAAT 3'). SD#4 has the same SD in the wild-type s10 RBS (5' AAGGAG 3') with an aligned spacing of 5 nucleotides (an actual spacing of 7 nucleotides because the SD only encompasses nucleotides 2 to 7, inclusive, of the full-SD) (5' ATATACA 3').

We used overlapping PCR primers to build the modified SD#1 sequence that was 5' to the 10A gene. The sequences for the 5' end primers were (in order of application):

| Name | Sequence | SEQ ID NO: |
|---|---|---|
| a-mut-s10SD#1 | 5' taacttta aggaggt ataat atgg ctagcatgac tggtg 3' | 26 |
| b-mut-s10SD#1 | 5' aataattttg tttaacttta aggaggt ataat atgg c 3' | 27 |
| c-mut-s10SD#1 | 5' tccctctaga aataattttg tttaacttta aggaggt a 3' | 28 |

We used overlapping PCR primers to build the modified SD#2 sequence that was 5' to the 10A gene. The sequences for the 5' end primers were (in order of application):

| Name | Sequence | SEQ ID NO: |
|---|---|---|
| a-mut-s10SD#2 | 5' taacttta aggaggt aGaat atgg ctagcatgac tggtg 3' | 29 |
| b-mut-s10SD#2 | 5' aataattttg tttaacttta aggaggt aGaat atgg c 3' | 30 |
| c-mut-s10SD#1 (same as above) | 5' tccctctaga aataattttg tttaacttta aggaggt a 3' | 31 |

We used overlapping PCR primers to build the modified SD#3 sequence that was 5' to the 10A gene. The sequences for the 5' end primers were (in order of application):

| Name | Sequence | SEQ ID NO: |
|---|---|---|
| a-mut-s10SD#3 | 5' cttta agaaggag AAAGAAT atgg ctagcatgac tggtg 3' | 32 |

-continued

| Name | Sequence | SEQ ID NO: |
|---|---|---|
| b-mut-s10SD#3 | 5' taattttg tttaacttta agaaggag AAAGAAT atgg 3' | 33 |
| c-mut-s10SD#3 | 5' tccctctaga aataattttg tttaacttta agaaggag 3' | 34 |

We used overlapping PCR primers to build the modified SD#4 sequence that was 5' to the 10A gene. The sequences for the 5' end primers were (in order of application):

| Name | Sequence | SEQ ID NO: |
|---|---|---|
| a-mut-s10SD#4 | 5' cttta agaaggag ATATACA atgg ctagcatgac tggtg 3' | 35 |
| b-mut-s10SD#4 | 5' taattttg tttaacttta agaaggag ATATACA atgg 3' | 36 |
| c-mut-s10 SD#3 (same as above) | 5' tccctctaga aataattttg tttaacttta agaaggag 3' | 37 |

We used several 3' end primers to introduce the HindIII site depending on melting temperatures needed to match the 5' primer:

| Name | Sequence | SEQ ID NO: |
|---|---|---|
| 10A-rev-med | 5' ctgc AAGCTT TTATTCCACTTTAA AG 3' | 38 |
| 10A-rev-short | 5' ctgc AAGCTT TTATTCCACTTTA 3' | 39 |
| 10A-rev-long | 5' ctgc AAGCTT TTATTCCACTTTAA AGACCAC 3' | 40 |
| 10A-rev-longer | 5' ctgc AAGCTT TTATTCCACTTTAA AGACCACTGC 3' | 41 |

Other Constructs:

Introducing Two Copies of Gene 10A into T7select 10-3b: In order to be able to introduce two copies of the 10A gene into T7select 10-3b in case one copy is inadequate, we designed primers with PvuI sites to allow two copies of 10A to be ligated together.

We used several 3' end primers to introduce the PvuI site to the 3' end of the first copy of the 10A gene depending on melting temperatures needed to match the 5' primer (which could be any of the 5' primers described in Constructs I, II, and III to create EcoRI-BsiWI-SexAI-φ10-s10-10A-PvuI, EcoRI-BsiWI-SexAI-s10-10A-PvuI, or EcoRI-BsiWI-SexAI-φ10-s10-10A-PvuI with modified RBS):

| Name | Sequence | SEQ ID No: |
|---|---|---|
| 10A-r-PvuI-long | 5' ctgc CGATCG TTATTCCACTTTAA AGACCAC 3' | 42 |
| 10A-r-PvuI-longer | 5' ctgc CGATCG TTATTCCACTTTAA AGACCACTGC 3' | 43 |

The 2nd copy of the 10A gene could be either PvuI-φ10-s10-10A-HindIII or PvuI-s10-10A-HindIII. For both cases, the 3' end primer used was either 10A-rev-med, 10A-rev-short, 10A-rev-long, or 10A-rev-longer depending on the melting temperatures needed to match the 5' primer. For the former case, we used the following 3' end primer in a PCR reaction starting off with the template being the PCR product from using 5' primer a-10Aphi10s10 with 3' primer 10A-rev-longer:

| Name | Sequence | SEQ ID NO: |
|---|---|---|
| b-PvuI-10Aphi10s10 | 5' gcat C GAT CG c TAA gTA AcT AA cgaaattaat acgactc 3' | 44 |

For the latter case, we used the following 3' end primers in sequential PCR reactions starting off with the template being the PCR product from using 5' primer b-10As10 with 3' primer 10A-rev-longer with the template being the PCR product from using 5' primer a-10As10 with 3' primer 10A-rev-longer:

| Name | Sequence | SEQ ID NO: |
|---|---|---|
| c-PvuI(1/2)-10As10 | 5' CG c TAA gTA AcT AA aataattttg tttaacttta ag 3' | 45 |
| d-PvuI(2/2)-10As10 | 5' gcat C GAT CG c TAA gTA AcT AA aataattttg t 3' | 46 |

We also created the option of inserting the transcriptional terminator Tφ in between the first and second copies of the 10A gene. This was accomplished by amplifying Tφ from wild-type T7 nucleotides 24107 to 24229 using a 5' end primer with a PvuI site and a 3' end primer with a SexAI site shown here:

| Name | Sequence | SEQ ID NO: |
|---|---|---|
| f-PvuI-Tphi | 5' gcat C GAT CG ctgc taacaaa cgaaaggaag c 3' | 47 |
| r-SexAI-Tphi | 5' ctgc AC CAG GT atatagttc ctcctttcag caaaaac 3' | 48 |

We designed many different constructs that could be pieced together in many combinations to express the 10A gene with varying efficiency.

From Construct I, we created EcoRI-BsiWI-SexAI-φ10-s10-10A-HindIII. From Construct II, we created EcoRI- BsiWI-SexAI-s10-10A-HindIII. In Construct III, we created four different versions of EcoRI-BsiWI-SexAI-φ10-s10-10A-HindIII with different Shine-Delgarno sequences with different spacers between the SD sequences and the translational start codon. If used the primers described in Construct III were used with the primers described in Construct II, we could create four different versions of EcoRI-BsiWI-SexAI-s10-10A-HindIII with the four different SD sequences and different spacers as well.

Finally, the primers in "Other Constructs" section as described above can also be used to create at least the following constructs: EcoRI-BsiWI-SexAI-φ10-s10-10A-PvuI-φ10-s10-10A-HindIII; EcoRI-BsiWI-SexAI-φ10-s10-10A-PvuI-s10-10A-HindIII; EcoRI-BsiWI-SexAI-s10-10A-PvuI-φ10-s10-10A-HindIII; EcoRI-BsiWI-SexAI-s10-10A-PvuI-s10-10A-HindIII; EcoRI-BsiWI-SexAI-φ10-s10-10A-PvuI-Tφ-SexAI-φ10-s10-10A-HindIII; EcoRI-BsiWI-SexAI-φ10-s10-10A-PvuI-Tφ-SexAI-s10-10A-HindIII; EcoRI-BsiWI-SexAI-s10-10A-PvuI-φ10-Tφ-SexAI-s10-10A-HindIII; EcoRI-BsiWI-SexAI-s10-10A-PvuI-Tφ-SexAI-s10-10A-HindIII.

In addition, the primers described in "Construct III" section can be used to permute any of the SD sequences in the various combinations described above to modified SD#1, SD#2, SD#3, or SD#4.

Engineering T7select 10-3b to Produce T3 Gene 1.2: Wild-type T7 does not productively infect male (F plasmid-containing) E. coli because of interactions between the F plasmid protein PifA and T7 genes 1.2 or 10 (3). F plasmid-containing E. coli infected by T7 die but do not lyse or release large numbers of T7 (3). Wild-type T3 grows normally on male cells because of T3's gene 1.2 product (3). When T3 gene 1.2 is expressed in wild-type T7, T7 is able to productively infect male cells (3). Because many biofilm-producing E. coli contain the F plasmid (4), it is important for our engineered phage to be able to productively infect male cells. Therefore, we decided to adapt the modification described by Garcia and Molineux (3) to express T3 gene 1.2 in T7.

Garcia and Molineux cloned T3 nucleotides 6127 to 6546 into the unique T7 BclI site located within T7 gene 1.7 at base pair 8311 in wild-type T7 and at base pair 6143 in wild-type T7 (3,5). We chose to either clone T3 nucleotides 6082 to 6500 or T3 nucleotides 6082 to 6555 into the unique T7 BclI site. The former construct (T3 by 6082-6500) does not include the RNaseIII recognition site R1.3 while the latter construct (T3 by 6082-6555) does include most of the RNase III recognition site. Note that these nucleotides include the complete coding sequence for T7 gene 1.1 as well, but that Garcia and Molineux did not.

We used the following 5' primers, which contains a BclI site, to isolate T3 gene 1.2 from nucleotides 6082 to 6500 or 6555.

| Name | Sequence | SEQ ID NO: |
|---|---|---|
| BclI - T3g1.2-forw | 5' gtca TGA TCA atgcgtacc aactttgaga aatttacc 3' | 49 |
| BclI + 1-T3g1.2-forw | 5' gtca TGA TCA t atgcgtacc aactttgaga aatttacc 3' | 50 |
| BclI + 2-T3g1.2-forw | 5' gtca TGA TCA tt atgcgtacc aactttgaga aatttacc 3' | 51 |

We used the following 3' primer, which contains a BclI site, to isolate T3 gene 1.2 from nucleotides 6082 to 6500.

| Name | Sequence | SEQ ID NO: |
|---|---|---|
| T3g1.2-BclI-rev | 5' cgta TGA TCA ttacttccag tgtttcaatt cgctg 3' | 52 |

We used the following 3' primer, which contains a BclI site, to isolate T3 gene 1.2 from nucleotides 6082 to 6555.

| Name | Sequence | SEQ ID NO: |
|---|---|---|
| T3g1.2-RNaseIII-BclI-rev | 5' cgta TGA TCA tcacg aaggccactc gttaaag 3' | 53 |

Garcia and Molineux describe a mutant T7 ST16 which had genes 1.1 and 1.2 deleted, that showed a higher plating efficiency and burst size when the T3 gene 1.2 was cloned into the BclI site compared with wild-type T7 with the same insertion [3]. ST16 was created by replacing wild-type T7 nucleotides 5947-6937 with the linker sequence 5' ggatccccgggagctc 3' (SEQ ID NO: 55) [5]. T7 with this deletion can also be used.

Engineering T7select 10-3b to Express Dispersin B to Degrade β-1,6-acetyl-D-glucosamine: Because of the highly specific activity of depolymerase enzymes, the 10B-cellulase fusion protein should equip our engineered T7 phage with the ability to degrade only cellulose polymers. E. coli biofilms, however, have been found to contain a heterogenous mix of polymers including cellulose (6), colanic acid (7), and β-1,6-acetyl-D-glucosamine (8), as well as extracellular appendages such as pili (9) and type II fimbriae (10).

By targeting another connective fiber either alone or in conjuction with cellulose, we hope to improve the biofilm-degrading performance of enzymatically-active T7. Derived from A. actinomycetemcomitans HK1651, dspB codes for dispersin B, a 381 amino-acid protein found to depolymerize β-1,6-acetyl-D-glucosamine (11,12). This gene was cloned by PCR, using forward primer 5'-GGGAATTCXATGAAT-TATATTAAGAAAATTATTTT-3' (SEQ ID NO: 56) (EcoRI site in bold) and reverse primer 5'-TTACCTGGTCTCACT-CAT CCCCATTCGTCTTAT G-3' (SEQ ID NO: 57) (SexAI site in bold), and inserted into the T7 genome in frame at the end of a truncated 10B capsid gene sequence, following amino acid 348.

Resulting 10B-DspB fusion proteins are incorporated into the phage capsid alongside the smaller 10A capsid proteins during phage assembly, giving rise to a T7 enhanced with the capacity to depolymerize β-1,6-acetyl-D-glucosamine. In order to modulate assembly efficiency, this 10B-DspB construct can be inserted in conjunction with any of the aforementioned 10A insert schemes.

Figure 5:
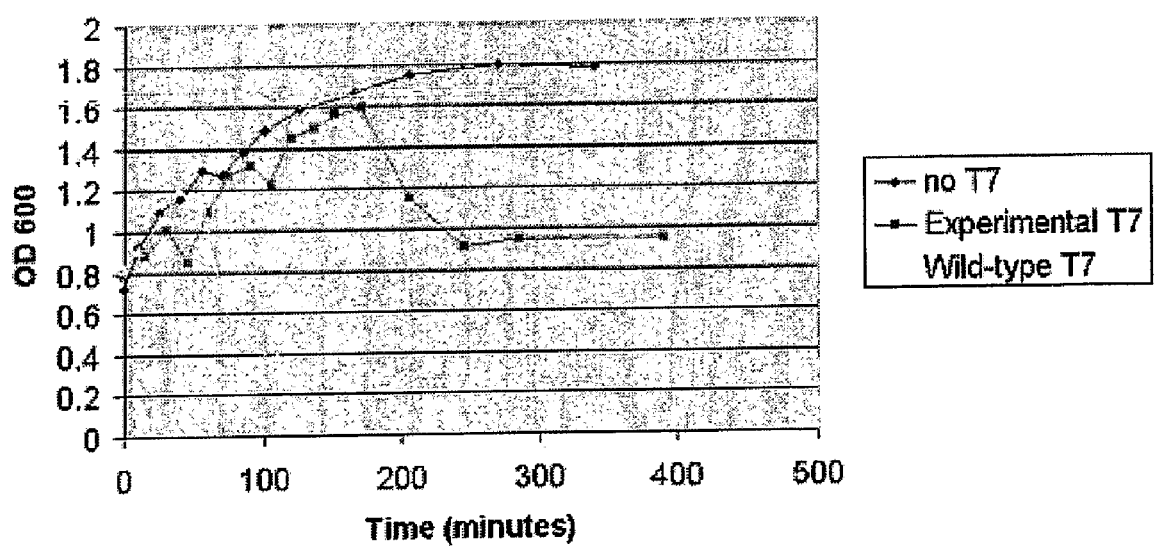
FIG. 5 shows T7 lysis of log-phase *E. coli* strain MG1655 (LacI::Kan) growing in LB. 40,000 PFU added to 35 mL of culture at OD approximately 0.8. Experimental T7 contains sequences for both 10A and 10B-dspB genes, while MG1655 has no 10A-producing plasmid.
Figure 6:
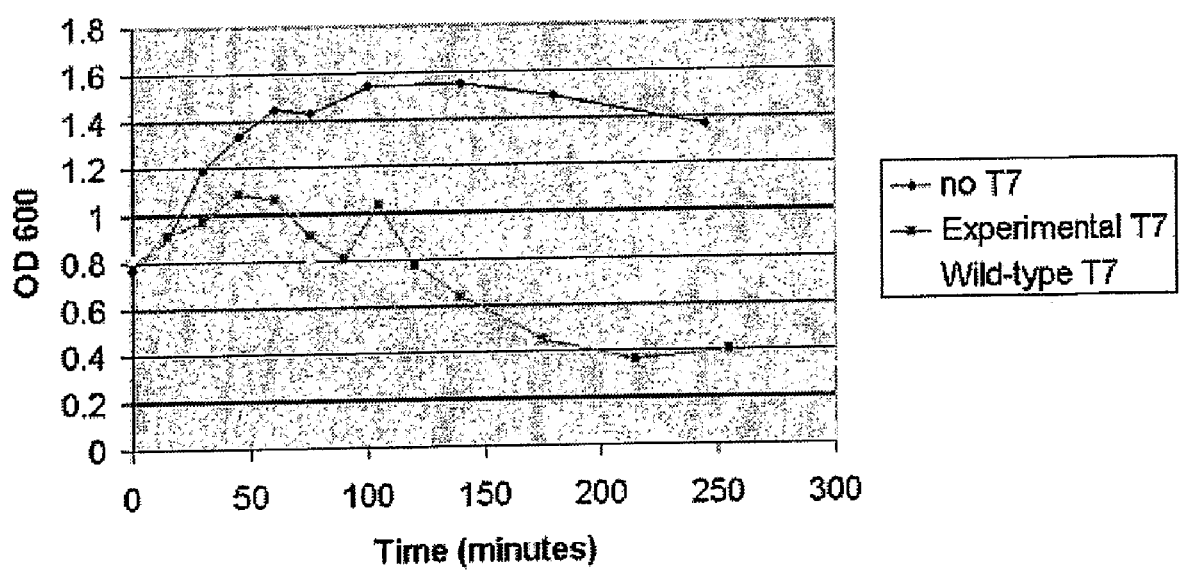
FIG. 6 shows T7 lysis of log-phase *E. coli* strain BLT5403 growing in LB. 40,000 PFU added to 35 mL of culture at OD approximately 0.8. Experimental T7 contains sequences for both 10A and 10B-dspB genes, and BLT5403 contains 10A-producing plasmid.

FIG. 5 shows T7 lysis of log-phase E. coli strain MG1655 (LacI::Kan) growing in LB. 40,000 PFU added to 35 mL of culture at OD approximately 0.8. Experimental T7 contains sequences for both 10A and 10B-dspB genes, while MG1655 has no 10A-producing plasmid. FIG. 6 shows T7 lysis of log-phase E. coli strain BLT5403 growing in LB. 40,000 PFU added to 35 mL of culture at OD approximately 0.8. Experimental T7 contains sequences for both 10A and 10B-dspB genes, and BLT5403 contains 10A-producing plasmid.

REFERENCES FOR EXAMPLE 2

1. Condron, B. G., Atkins, J. F., and Gesteland, R. F. 1991. Frameshifting in gene 10 of bacteriophage T7. J. Bacteriol. 173:6998-7003.

2. U.S. Pat. No. 5,766,905. 1998. Cytoplasmic bacteriophage display system.
3. Garcia, L. R., and Molineux, I. J. 1995. Incomplete entry of bacteriophage T7 DNA into F plasmid-containing *Escherichia coli*. J. Bacteriol. 177:4077-4083.
4. Ghigo, J. M. 2001. Natural conjugative plasmids induce bacterial biofilm development. Nature. 412:442-445.
5. Molineux, I. J. 2005. Personal communication.
6. Zogaj, X., Bokranz, W., Nimtz, M., Romling, U. 2003. Production of Cellulose and Curli Fimbriae by Members of the Family Enterobacteriaceae Isolated from the Human Gastrointestinal Tract. Infect. Immun. 71(7): 4151-4158.
7. Danese, P. N., Pratt, L. A., Kolter, R. 2000. Exopolysaccharide production is required for development of *Escherichia coli* K-12 biofilm architecture. J. Bacteriol. 182: 3593-3596.
8. Wang, X., Preston, J F., Romeo, T. 2004. The pgaABCD Locus of *Escherichia coli* Promotes the Synthesis of a Polysaccharide Adhesin Required for Biofilm Formation. J. Bacteriol. 186(9): 2724-2734.
9. Reisner, A., Haagensen, J. A. J., Schembri, M. A., Zechner E. L., Molin, S. 2003. Development and maturation of *Escherichia coli* K-12 biofilms. Mol. Microbiol. 48(4): 933-946.
10. Sheikh, J., Hicks, S., Dall; Agnol, M., Phillips, A. D., Nataro, J. P. 2001. Roles for F is and YafK in biofilm formation by enteroaggregative *Escherichia coli*. Mol. Microbiol. 41(5): 983-987.
11. Itoh, Y., Wang, X., Hinnebusch, B. J., Preston, J. F., Romeo, T. 2005. Depolymerization of β-1,6-acetyl-D-glucosamine Disrupts the Integrity of Diverse Bacterial Biofilms. J. Bacteriol. 187: 382-387.
12. Kaplan, J. B., Ragunath, C., Ramasubbu, N., Fine, D. H. 2003. Detachment of *Actinobacillus* actinomycetemcomitans Biofilm Cells by an Endogenous β-Hexosaminidase Activity. J. Bacteriol. 185(16): 4693-4698.

SEQUENCE LISTING

The instant application contains a Sequence Listing which has been submitted in ASCII format via EFS-Web and is hereby incorporated by reference in its entirety. Said ASCII copy, created on Feb. 6, 2012, is named 71586782.txt and is 16,539 bytes in size.

We claim:

1. A method of degrading biofilm, comprising:
   contacting the biofilm with a genetically engineered bacteriophage;
   wherein the genetically engineered bacteriophage is self-replicating and capable of assembly upon infection of a target cell;
   wherein the genetically engineered bacteriophage encodes i) a wild type bacteriophage capsid protein and ii) at least one fusion protein comprising a biofilm degrading enzyme attached to a bacteriophage capsid protein; and
   wherein, the biofilm degrading enzyme is displayed on the surface of the bacteriophage.

2. The method of claim 1, wherein the biofilm is a dual biofilm.

3. The method of claim 1, wherein the biofilm is formed by more than one bacterial strain.

4. The method of claim 1, wherein the bacteriophage is a lambda phage.

5. The method of claim 1, wherein the bacteriophage is selected from T2, T3, T4, and T7.

6. The method of claim 5, wherein the bacteriophage is T7.

7. The method of claim 6, wherein the bacteriophage is T7 10-3b-genetically engineered to express 10A capsid protein as the wild type bacteriophage capsid protein.

8. The method of claim 1, wherein the bacteriophage is Pf1.

9. The method of claim 1, wherein the at least one enzyme is selected from a cellulase, a polyglucosamine (PGA) depolymerase, and a colonic acid depolymerase.

10. The method of claim 9, wherein the cellulase is cellulase A.

11. The method of claim 9, wherein the colonic acid depolymerase is selected from 1,4-L-fucodise hydrolase, depolymerizing alginase, and DNase I.

12. The method of claim 1, wherein the biofilm is contacted with at least two different genetically engineered enzyme displaying bacteriophages.

13. The method of claim 12, wherein the at least two different genetically engineered bacteriophages display different biofilm degrading enzymes on their surface.

14. The method of claim 12, wherein the at least two different genetically engineered bacteriophages are obtained by genetic modification of different wild type phage strains.

15. The method of claim 1, wherein the bacteriophage displays 1-20 enzyme copies on the bacteriophage capsid.

16. The method of claim 1, wherein the bacteriophage displays 5-15 enzyme copies on the bacteriophage capsid.

17. The method of claim 1, wherein the bacteriophage displays 20-500 enzyme copies on the bacteriophage capsid.

18. The method of claim 1, wherein the bacteriophage further comprises all the essential genes for virus replication in the naturally occurring target bacterial strain.

* * * * *

```
                              SEQUENCE LISTING

<160> NUMBER OF SEQ ID NOS: 57

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catgaattct gcaggtgtgc cttttaacac aaaatac                              37

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacgtcaagc tttttccgta aatctgtcaa aaacccatta ca                        42

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtaactaacg aaattaatac gactcactat agg                                  33

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 4
cctggtctaa gtaactaacg aaattaatac gactc                                      35

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctaagtaact aacctggtct aagtaactaa cgaa                                       34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgtcgtacg ctaagtaact aacctggtct aagt                                       34

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcatgaattc aggtgtcgta cgctaagtaa cta                                        33

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgcaagctt ttattccact ttaaag                                                26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgcaagctt ttattccact tta                                                   23

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
ctgcaagctt ttattccact ttaaagacca c                                31
```

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 11

```
ctgcaagctt ttattccact ttaaagacca ctgc                             34
```

<210> SEQ ID NO 12
<211> LENGTH: 1186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
gcatgaattc aggtgtcgta cgctaagtaa ctaacctggt ctaagtaact aacgaaatta    60
atacgactca ctatagggag accacaacgg tttccctcta gaataatttt gtttaactt    120
taagaaggag atatacatat ggctagcatg actggtggac agcaaatggg tactaaccaa   180
ggtaaaggtg tagttgctgc tggagataaa ctggcgttgt tcttgaaggt atttggcggt   240
gaagtcctga ctgcgttcgc tcgtacctcc gtgaccactt ctcgccacat ggtacgttcc   300
atctccagcg gtaaatccgc tcagttccct gttctgggtc gcactcaggc agcgtatctg   360
gctccgggcg agaacctcga cgataaacgt aaggacatca acacaccga gaaggtaatc    420
accattgacg gtctcctgac ggctgacgtt ctgatttatg atattgagga cgcgatgaac   480
cactacgacg ttcgctctga gtatacctct cagttgggtg aatctctggc gatggctgcg   540
gatggtgcgg ttctggctga gattgccggt ctgtgtaacg tggaaagcaa atataatgag   600
aacatcgagg gcttaggtac tgctaccgta attgagacca ctcagaacaa ggccgcactt   660
accgaccaag ttgcgctggg taaggagatt attgcggctc tgactaaggc tcgtgcggct   720
ctgaccaaga actatgttcc ggctgctgac cgtgtgttct actgtgaccc agatagctac   780
tctgcgattc tggcagcact gatgccgaac gcagcaaact acgctgctct gattgaccct   840
gagaagggtt ctatccgcaa cgttatgggc tttgaggttg tagaagttcc gcacctcacc   900
gctggtggtg ctggtaccgc tcgtgagggc actactggtc agaagcacgt cttccctgcc   960
aataaaggtg agggtaatgt caaggttgct aaggacaacg ttatcggcct gttcatgcac  1020
cgctctgcgg taggtactgt taagctgcgt gacttggctc tggagcgcgc tcgccgtgct  1080
aacttccaag cggaccagat tatcgctaag tacgcaatgg ccacggtgg tcttcgccca   1140
gaagctgctg gtgcagtggt ctttaaagtg gaataaaagc ttgcag                 1186
```

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 13

```
ctaaaataat tttgtttaac tttaagaagg agat                              34
```

```
<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtaactaaaa taattttgtt taactttaag aagg                              34

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtctaagtaa ctaaaataat tttgtttaac tttaag                            36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acctggtcta agtaactaaa ataattttgt ttaact                            36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctaagtaact aacctggtct aagtaactaa aataat                            36

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtgtcgtacg ctaagtaact aacctggtct aagt                              34

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcatgaattc aggtgtcgta cgctaagtaa cta                               33

<210> SEQ ID NO 20
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgcaagctt ttattccact ttaaag                                          26

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctgcaagctt ttattccact tta                                             23

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgcaagctt ttattccact ttaaagacca c                                    31

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctgcaagctt ttattccact ttaaagacca ctgc                                 34

<210> SEQ ID NO 24
<211> LENGTH: 1136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gcatgaattc aggtgtcgta cgctaagtaa ctaacctggt ctaagtaact aaaataattt      60
tgtttaactt taagaaggag atatacatat ggctagcatg actggtggac agcaaatggg     120
tactaaccaa ggtaaaggtg tagttgctgc tggagataaa ctggcgttgt tcttgaaggt     180
atttggcggt gaagtcctga ctgcgttcgc tcgtacctcc gtgaccactt ctcgccacat     240
ggtacgttcc atctccagcg gtaaatccgc tcagttccct gttctgggtc gcactcaggc     300
agcgtatctg ctccgggcg agaacctcga cgataaacgt aaggacatca aacacaccga     360
gaaggtaatc accattgacg gtctcctgac ggctgacgtt ctgatttatg atattgagga     420
cgcgatgaac cactacgacg ttcgctctga gtatacctct cagttgggtg aatctctggc     480
gatggctgcg gatggtgcgg ttctggctga gattgccggt ctgtgtaacg tggaaagcaa     540
atataatgag aacatcgagg gcttaggtac tgctaccgta attgagacca ctcagaacaa     600
```

-continued

```
ggccgcactt accgaccaag ttgcgctggg taaggagatt attgcggctc tgactaaggc    660
tcgtgcggct ctgaccaaga actatgttcc ggctgctgac cgtgtgttct actgtgaccc    720
agatagctac tctgcgattc tggcagcact gatgccgaac gcagcaaact acgctgctct    780
gattgaccct gagaagggtt ctatccgcaa cgttatgggc tttgaggttg tagaagttcc    840
gcacctcacc gctggtggtg ctggtaccgc tcgtgagggc actactggtc agaagcacgt    900
cttccctgcc aataaaggtg agggtaatgt caaggttgct aaggacaacg ttatcggcct    960
gttcatgcac cgctctgcgg taggtactgt taagctgcgt gacttggctc tggagcgcgc   1020
tcgccgtgct aacttccaag cggaccagat tatcgctaag tacgcaatgg ccacggtgg   1080 tcttcgccca gaagctgctg gtgcagtggt ctttaaagtg aataaaagc ttgcag       1136
```

<210> SEQ ID NO 25
<211> LENGTH: 9
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 taaggaggt                                                              9

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taactttaag gaggtataat atggctagca tgactggtg                             39

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aataattttg tttaacttta aggaggtata atatggc                               37

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tccctctaga aataattttg tttaacttta aggagta                               38

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 29
taactttaag gaggtagaat atggctagca tgactggtg                                  39

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aataattttg tttaacttta aggaggtaga atatggc                                    37

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tccctctaga aataattttg tttaacttta aggaggta                                   38

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctttaagaag gagaaagaat atggctagca tgactggtg                                  39

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
taattttgtt taactttaag aaggagaaag aatatgg                                    37

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tccctctaga aataattttg tttaacttta agaaggag                                   38

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
ctttaagaag gagatataca atggctagca tgactggtg                    39
```

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
taatttgtt taactttaag aaggagatat acaatgg                       37
```

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
tccctctaga aataattttg tttaacttta agaaggag                     38
```

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
ctgcaagctt ttattccact ttaaag                                  26
```

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
ctgcaagctt ttattccact tta                                     23
```

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
ctgcaagctt ttattccact ttaaagacca c                            31
```

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
ctgcaagctt ttattccact ttaaagacca ctgc                         34
```

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgccgatcg ttattccact ttaaagacca c                              31

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctgccgatcg ttattccact ttaaagacca ctgc                           34

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcatcgatcg ctaagtaact aacgaaatta atacgactc                      39

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgctaagtaa ctaaaataat tttgtttaac tttaag                         36

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcatcgatcg ctaagtaact aaaataattt tgt                            33

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcatcgatcg ctgctaacaa acgaaaggaa gc                             32

<210> SEQ ID NO 48

-continued

<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctgcaccagg tatatagttc ctcctttcag caaaaac                              37

<210> SEQ ID NO 49
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtcatgatca atgcgtacca actttgagaa atttacc                              37

<210> SEQ ID NO 50
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtcatgatca tatgcgtacc aactttgaga aatttacc                             38

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtcatgatca ttatgcgtac caactttgag aaatttacc                            39

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgtatgatca ttacttccag tgtttcaatt cgctg                                35

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgtatgatca tcacgaaggc cactcgttaa ag                                   32

<210> SEQ ID NO 54
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid or not present
<220> FEATURE:
<221> NAME/KEY: MOD_RES
<222> LOCATION: (14)..(15)
<223> OTHER INFORMATION: Any amino acid or not present

<400> SEQUENCE: 54

Xaa Xaa Xaa Ser Glu Gly Gly Gly Ser Glu Gly Gly Gly Xaa Xaa
1               5                   10                  15

<210> SEQ ID NO 55
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggatccccgg gagctc                                                    16

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other

<400> SEQUENCE: 56
gggaattcna tgaattatat taagaaaatt atttt                               35

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttacctggtc tcactcatcc ccattcgtct tatg                                34
```